US007098195B2

(12) United States Patent
Sackstein et al.

(10) Patent No.: US 7,098,195 B2
(45) Date of Patent: Aug. 29, 2006

(54) FLUORINATED GLUCOSAMINE ANALOGS USEFUL FOR MODULATING POST-TRANSLATIONAL GLYCOSYLATIONS ON CELLS

(75) Inventors: Robert Sackstein, Sudbury, MA (US); Charles J. Dimitroff, Williamsville, NY (US); Ralph J. Bernacki, Elma, NY (US); Moheswar Sharma, Amherst, NY (US); Khushi L. Matta, Williamsville, NY (US); Brajeswar Paul, Williamsville, NY (US)

(73) Assignees: Health Research, Inc., Buffalo, NY (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 10/305,812

(22) Filed: Nov. 26, 2002

(65) Prior Publication Data

US 2003/0148997 A1    Aug. 7, 2003

Related U.S. Application Data

(60) Provisional application No. 60/334,151, filed on Nov. 28, 2001.

(51) Int. Cl.
  *A61K 31/7008* (2006.01)
  *A61K 31/573* (2006.01)
  *A61K 31/415* (2006.01)
  *A61K 31/192* (2006.01)

(52) U.S. Cl. .................. 514/62; 514/161; 514/171; 514/406; 514/570; 536/53; 435/7.24

(58) Field of Classification Search .................. 514/62, 514/161, 171, 406, 570; 536/53; 435/7.24
See application file for complete search history.

(56) References Cited

U.S. PATENT DOCUMENTS 5,627,290 A    5/1997  Iida et al. .................... 549/419

OTHER PUBLICATIONS

Alon R., et al., "Distinct Cell Surface Ligands Mediate T Lymphocyte Attachment and Rolling on P and E Selectin Under Physiological Flow," *J. Cell Biol.* 127(5):1485-1495 (1994).
Berg EL., et al., "The Cutaneous Lymphocyte Antigen is a Skin Lymphocyte Homing Receptor for the Vascular Lectin Endothelial Cell-Leukocyte Adhesion Molecule," *J. Exp. Med.* 174:1461-1466 (1991).
Bernacki RJ, et al., "Biochemical Characteristics, Metabolism, and Antitumor Activity of Severeral Acetylated Hexosamines," *J. Supramol. Struct.* 7(2):235-250 (1977).

Blander JM, et al., "$\alpha(1,3)$-Fucosyltransferase VII and $\alpha(2,3)$-Sialyltransferase IV are up-Regulated in Activated CD4 T Cells and Maintained After Their Differentiation Into Th1 and Migration Into Inflammatory Sites," *J. Immunology* 163(7):3746-3752 (1999).
Borges E., et al., "P-selectin Glycoprotein Ligand-1 (PSGL-1) on T Helper 1 But Not on T Helper 2 Cells Binds to P-Selectin and Supports Migration Into Inflamed Skin," *J. Biol. Chem.* 272(45):28786-28792 (1997).
Borowitz MJ., et al., "Abnormalities of Circulating T-cell Subpopulations in Patients with Cutaneous T-cell Lymphoma: Cutaneous Lymphocyte-Associated Antigen Expression on T Cells Correlates with Extent of Disease," *Leukemia* 7(6):859-863 (1993).
Burdick MM, et al., "Glycolipids Support E-selectin-Specific Strong Cell Tethering Under Flow," *Biochem. Biophys. Res. Commun.* 284(1):42-49 (2001).
Davis RE, et al., "T-Lymphocytes Expressing HECA-452 Epitope are Present in Cutaneous Acute Graft-Versus-Host Disease and Erythema Multiforme, but not in Acute Graft-Versus-Host Disease in Gut Organs," *Amer. J. Path.* 141(3):691-698 (1992).
Dimitroff CJ, et al., "A Distinct Glycoform of CD44 is an L-Selectin Ligand on Human Hematopoietic Progenitor Cells," *Proc. Natl. Acad. Sci.* 97(25), 13841-13846 (2000).
Dimitroff CJ, et al., "CD44 is a Major E-Electin Ligand on Human Hematopoietic Progenitor Cells," *J Cell Biol.* 153:1277-1286 (2001).
Dimitroff CJ, et al., "Differential L-Selectin Binding Activities of Human Hematopoietic Cell L-Selectin Ligands, HCELL and PSGL-1," *J. Biol. Chem.* 276(50):47623-47631 (2001).
Ellies LG, et al., "Core 2 Oligosaccharide Biosynthesis Distinguishes Between Selectin Ligands Essential for Leukocyte Homing and Inflammation," *Immunity* 9(6):881-890 (1998).
Erdmann I, et al., "Fucosyltransferase VII-Deficient Mice with Defective E-, P-, and L-Selectin Ligands Show Impaired CD4+ and CD8+ T Cell Migration Into the Skin, But Normal Extravasation Into Visceral Organs." *J. Immunol.* 168(5):2139-2146 (2002).
Fuhlbrigge RC, et al., "Cutaneous Lymphocyte Antigen is a Specialized Form of PSGL-1 Expressed on Skin-Homing T-Cells," *Nature* 389:978-981 (1997).
Heald PW, et al., "Skin-Selective Lymphocyte Homing Mechanisms in the Pathogenesis of Leukemic Cutaneous T-Cell Lymphoma," *J. Invest. Dermatol.* 101(2):222-226 (1993).
Homeister JW, et al., "The $\alpha(1,3)$Fucosyltransferases FucT-IV and FucT-VII Exert Collaborative Control Over Selectin-Dependent Leukocyte Recruitment and Lymphocyte Homing," *Immunity* 15(1):115-126 (2001).

(Continued)

*Primary Examiner*—Shaojia A. Jiang
*Assistant Examiner*—Ganapathy Krishnan
(74) *Attorney, Agent, or Firm*—Fish & Richardson P.C.

(57) ABSTRACT

The present invention provides compositions and methods for inhibiting cell migration, e.g., lymphocytes and inflammation. The invention also provides an improved process for preparing fluorinated N-acetylglucosamines.

26 Claims, 15 Drawing Sheets

OTHER PUBLICATIONS

Kieffer JD, et al., "Neutrophils, Monocytes, and Dendritic Cells Express the Same Specialized Form of PSGL-1 as Do Skin-Homing Memory T Cells: Cutaneous Lymphocyte Antigen," *Biochem. Biophys. Res. Commun.* 285(3):577-587 (2001).

Kuan SF, et al., "Inhibition of Mucin GLycosylation by Aryl-N-acetyl-α-galactosamides in Human Colon Cancer Cells," *J. Biol Chem.* 264(32):19271-19277 (1989).

Kumar R, et al., "Core2 β-1,6-N-Aacetylglucosaminyltransferase Eenzyme Aactivity is Critical for P-Selectin Glycoprotein Ligand-1 Binding to P-Selectin," *Blood* 88:3872-3879 (1996).

Lowe JB, et al., "ELAM-1-Dependent Cell Adhesion to Vascular Endothelium Determined by a Transfected Human Fucosyltransferase cDNA," *Cell.* 63(3):475-484 (1990).

Maemura K, et al., "Poly-N-Acetyllactosaminyl O-glycans Attached to Leukosialin. The Presence of Sialyl Le(x) Structures in O-glycans," *J. Biol. Chem.* 267(34):24379-24386 (1992).

Maly P, et al., "The α(1,3)Fucosyltransferase Fuc-TVII Controls Leukocyte Trafficking Through an Essential Role in L-, E-, and P-Selectin Ligand Biosynthesis," *Cell.* 86:643-653 (1996).

Mizukawa Y, et al., "Immunohistochemical Detection of Skin-Homing T Cells Expression Fucosyltransferase VII (Fuc-TVII) In Vitro and In Situ," *Lab. Invest.* 81(5):771-773 (2001).

Moore KL, et al., "The P-Selectin Glycoprotein Ligand From Human Neutrophils Displays Sialylated, Fucosylated, O-linked Poly-N-Acetyllactosamine," *J. Biol. Chem.* 269(37):23318-23327 (1994).

Nakamura M, et al. "UDP-GlcNAc:Galβ1→3GalNAc (GlcNAc to GalNAc) β1→6N-Acetylglucosaminyltransferase Holds a Key Role on the Control of CD15s Expression in Human Pre-B Lymphoid Cell Lines," *Glycobiology* 9(1):1-12 (1999).

Nakayama F, et al., "Expression of Cutaneous Lymphocyte-Associated Antigen Regulated by a Set of Glycosyltransferases in Human T Cells: Involvement of α1, 3-Fucosyltransferase VII and β1,4-Galactosyltransferase I," *J. Invest. Dermatol.* 115(2):299-306 (2000).

Niemela R, et al., "Complementary Acceptor and Site Specificities of Fuc-TIV and Fuc-TVII Allow Effective Biosynthesis of Sialyl-TriLex and Related Polylactosamines Present on Glycoprotein Counterreceptors of Selectins," *J. Biol. Chem.* 273(7):4021-4026 (1998).

Okajima T, et al. "Molecular Cloning of a Novel α2,3-Sialyltransferase (ST3Gal VI) That Sialylates Types II Lactosamine Structures on Glycoproteins and Glycolipids," *J. Biol. Chem.* 274(17):11479-11486 (1999).

Picker LJ, et al., "A Unique Phenotype of Skin-Associated Lymphocytes in Humans. Preferential Expression of the HECA-452 Epitope by Benign and Malignant T cells at Cutaneous Sites," *Amer. J. Path.* 136:1053-1068 (1990).

Picker LJ, et al., "Control of lymphocyte recirculation in man. II. Differential Regulation of the Cutaneous Lymphocyte-Associated Antigen, a Tissue-Selective Homing Receptor for Skin-Homing T Cells," *J. Immunol.* 150(3):1122-1136 (1993).

Piller F, et al., "Altered O-Glycan Synthesis in Lymphocytes from Patients with Wiskott-Aldrich Syndrome," *J Exp. Med.* 173(6):1501-1510 (1991).

Pinola M, et al., "Characterization of the E-Selectin Ligand on NK cells," *J. Immunol.* 152(7):3586-3594 (1994).

Robert C, et al., "Inflammatory Skin Diseases, T Cells, and Immune Surveillance," *New Engl. J. Med.* 341(24):1817-1828 (1999).

Rook AH, et al., "The Immunopathogenesis of Cutaneous T-Cell Lymphoma. Hemato," *Oncol. Clin. N. Amer.* 9:997-1010 (1995).

Rossiter H, et al., "Skin Disease-Related T-Cells Bind to Endothelial Selectins: Expression of Cutaneous Lymphocyte Antigen (CLA) Predicts E-Selectin But Not P-Selectin Binding," *Eur. J. Immuno.* 24:205-210 (1994).

Santamaria Babi LF, et al., "Circulating Allergen-Reactive T Cells from Patients With Atopic Dermatitis and Allergic Contact Dermatitis Express the Skin-Selective Homing Receptor, the Cutaneous Lymphocyte-Associated Antigen," *J. Exp. Med.* 181(5):1935-1940 (1995).

Sackstein R, et al., "A Hematopoietic Cell L-Selectin Ligand That is Distinct From PSGL-1 and Displays N-Glycan-Dependent Binding Activity," *Blood* 96:2765-2774 (2000).

Schmid K, et al., "Amino Acid Sequence of Human Plasma Galactoglycoprotein: Identity With the Extracellular Region of CD43 (Sialophorin)," *Proc. Natl. Acad. Sci. U S A.* 89(2):663-667 (1992).

Sharma and Korytnyk, "Modifications at C-3 and C-4 of 2 Amino-2-Deoxy-D-Glucose," *Carbohyd. Res.* 79:39-51 (1980).

Sharma M, et al., "Fluorinated Carbohydrates as Potential Plasma Membrane Modifiers. Synthesis of 4- and 6-Fluro Derivatives of 2-Acetamido-2-Deoxy-D-Hexopyranoses," *Carbohyd. Res.* 198:205-221 (1990).

Sigmundsdottir H, et al., "The Frequency of CLA+ CD8+ T cells in the Blood of Psoriasis Patients Correlates Closely with the Severity of Their Disease," *Clin Exp. Immunol.* 126(2):365-369 (2001).

Snapp KR, et al., "P-Selectin Glycoprotein Ligand-1 is Essential for Adhesion to P-Selectin but not E-Selectin in Stably Transfected Hematopoietic Cell Lines," *Blood* 89(3):896-901 (1997).

Snapp KR, et al., "Differential Requirements for the O-Linked Branching Enzyme Core 2 β1-6-N-Glucosaminyltransferase in Biosynthesis of Ligands for E-Selectin and P-Selectin," *Blood* 97(12):3806-3811 (2001.

Sperandio M, et al., "Severe Impairment of Leukocyte Rolling in Venules of Core 2 Glucosaminyltransferase-Deficient Mice," *Blood* 97(12):3812-3819 (2001).

Stroud MR, et al., "Monosialogangliosides of Human Myelogenous Leukemia HL60 Cells and Normal Human Leukocytes. 1. Separation of E-Selectin Binding from Nonbinding Gangliosides, and Absence of Sialosyl-Le(x) Having Tetraosyl to Octaosyl core," *Biochemistry* 35(3):758-769 (1996).

Tanaka Y, et al., "Distinct Phenotype of Leukemic T Cells With Various Tissue Tropisms," *J. Immunol.* 158(8):3822-3829 (1997).

Thomas et al., "Use of 2-Methyl-(3,6,di-0-acetyl-1,2,4-trideoxy-4-fluoro-α-D-glucopyrano)-[2,1-d]-2-oxazoline as a Glycosyl Donor. Synthesis of Benzyl 2-acetamido-6-0-[2-acetamido-2,4-dideoxy-4-fluro-α-D-glucopyranosyl)-2-deoxy-β-D-galactopyranoside," *Carbohyd. Res.* 175:153-157 (1988).

Tu L, et al., "L-Selectin Ligands Expressed by Human Leukocytes are HECA-452 Antibody-Defined Carbohydrate Epitopes Preferentially Displayed by P-selectin Glycoprotein Ligand-1," *J. Immunol.* 163(9):5070-5078 (1999).

Wagers AJ, et al., "An Important Role for the α 1,3 Fucosyltransferase, FucT-VII, in Leukocyte Adhesion to E-Selectin" *Blood,* 88(6):2125-2132 (1996).

Weninger W, et al. "Specialized Contributions by α(1,3)-Fucosyltransferase-IV and FucT-VII During Leukocyte Rolling in Dermal Microvessels," *Immunity* 12(6):665-676 (2000).

Woynarowska B, et al., "Inhibition of Lectin Mediated Ovarian Tumor Cell Adhesion by Sugar Analogs," *J. Biol. Chem.* 269(36):22797-22803 (1994).

Woynarowska B, et al., "Inhibition Human HT-29 colon carcinoma cell adhesion by a 4-Fluoro-Glucosamine Analogue," *Glycoconjugate J.* 13(4):663-674 (1996).

Zeng S, et al., "Complete Enzymatic Synthesis of the Mucin-Type Sialyl Lewis X Epitope, Involved in the Interaction Between PSGL-1 and P-Selectin," *GLycoconjugate J.* 16(9):487-97 (1999).

International Search Report for PCT/US02/38003 dated Dec. 23, 2003.

Abdel-Rahman "Synthesis of some 2-methylthiouracil nucleosides and its 5-halo analogues of 2-acetamido-2-deoxy-D-glucose" *Pharmazie* 56(10):773-776 (2001).

Berkin et al. "Synthesis of 4-deoxy-4-fluoro analogues of 2-acetamido-2-deoxy-D-glucose and 2-acetamido-2-deoxy-D-galactose and their effects on cellular glycosaminoglycan biosynthesis" *Carbohydrate Research* 326:250-263 (2000).

Figure 5A, B and C
A.
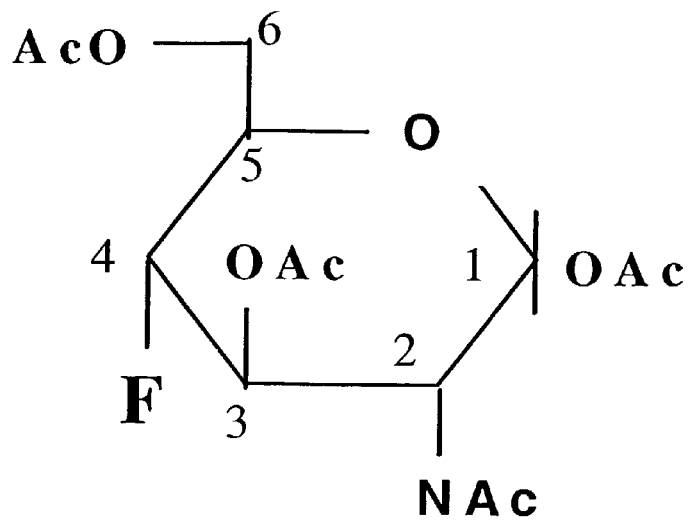
B.
- Proposed Site of 4-F-GlcNAc Incorporation
Poly-N-acetyllactosaminoglycans: (Galβ1, ↑4GlcNAcβ1,3)$_n$
C.
- Proposed Site of 4-F-GlcNAc Incorporation in Carbohydrate Selectin-Binding Determinants
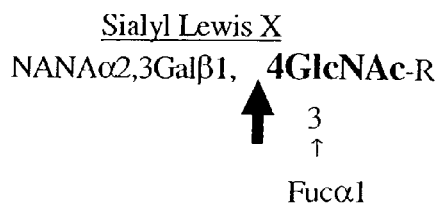
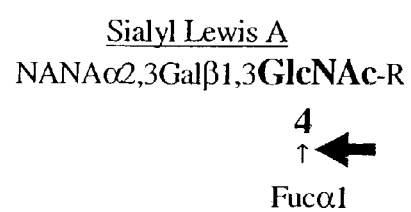

Figure 6A, B and C
A. CLA (PSGL-1)
(moAb HECA-452)
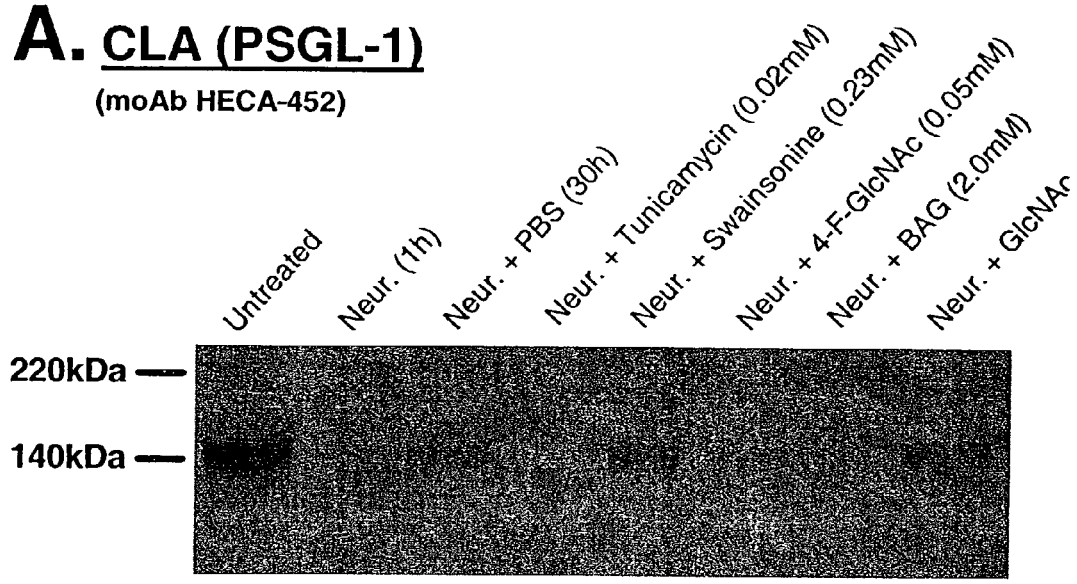
B. PSGL-1
(moAbs PL-1, 2G3 and 4D8)
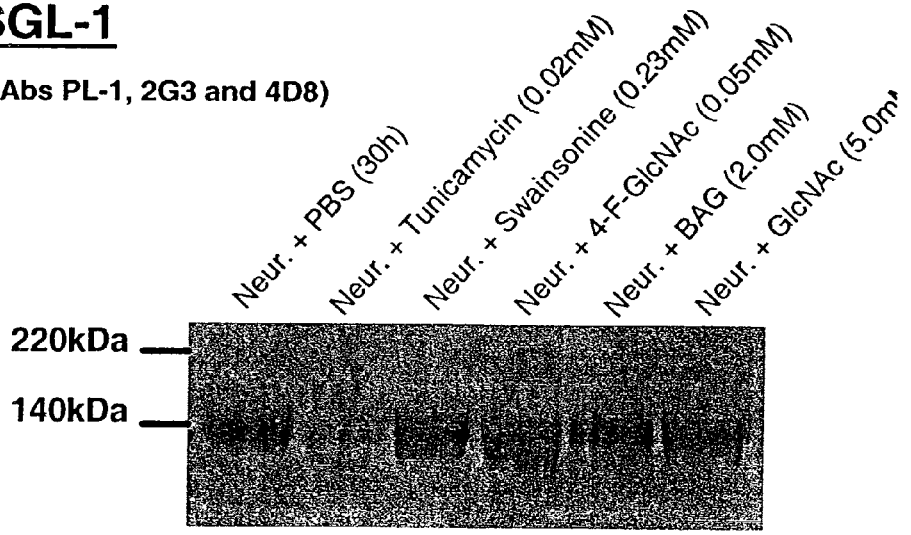
C. CD43
(moAb L60)
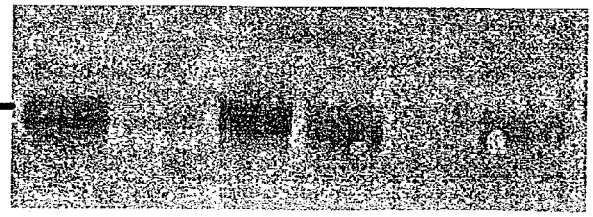

Figure 8A, B and C

Figure 9
A. FACS ASSESSMENT OF HECA-452 AND PSGL-1 EXPRESSION ON HUMAN T-CELLS AFTER BROMELAIN TREATMENT
<u>Cell Staining</u> (% Positive (MCF))
|  | CLA$^+$ T-cells | | CLA$^{low}$ T-cells | |
| --- | --- | --- | --- | --- |
|  | Untreated | Bromelain | Untreated | Bromelain |
| Anti-CLA (moAb HECA-452) | 99% (2304) | 68% (1869) | 18% (51) | 16% (48) |
| Anti-PSGL-1 (moAb PL-2) | 99% (97) | 1% (10) | 96% (105) | 0% (25) |
B.
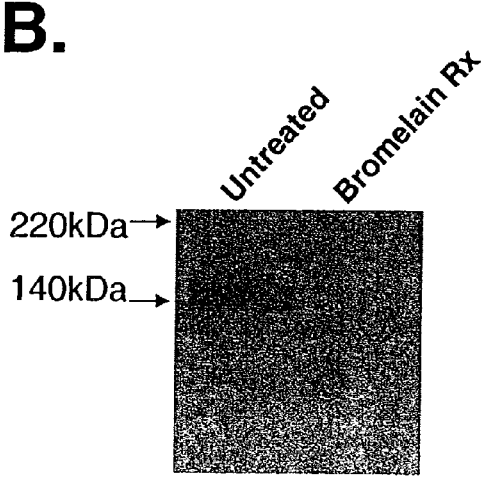
Anti-PSGL-1 Immunoblot
C.
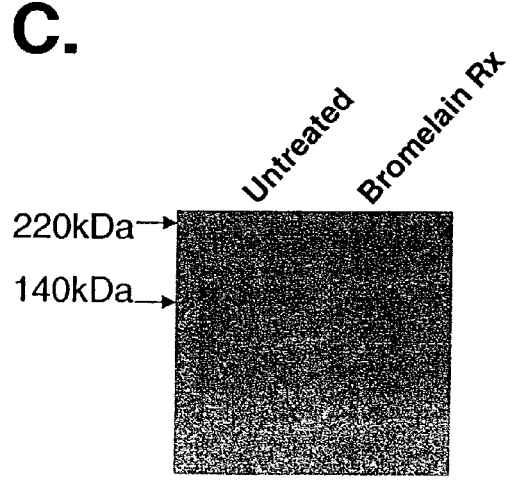
HECA-452 Immunoblot Figure 11
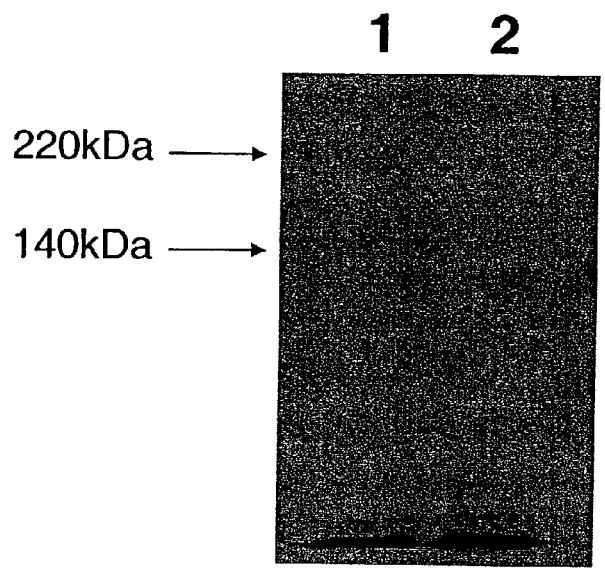
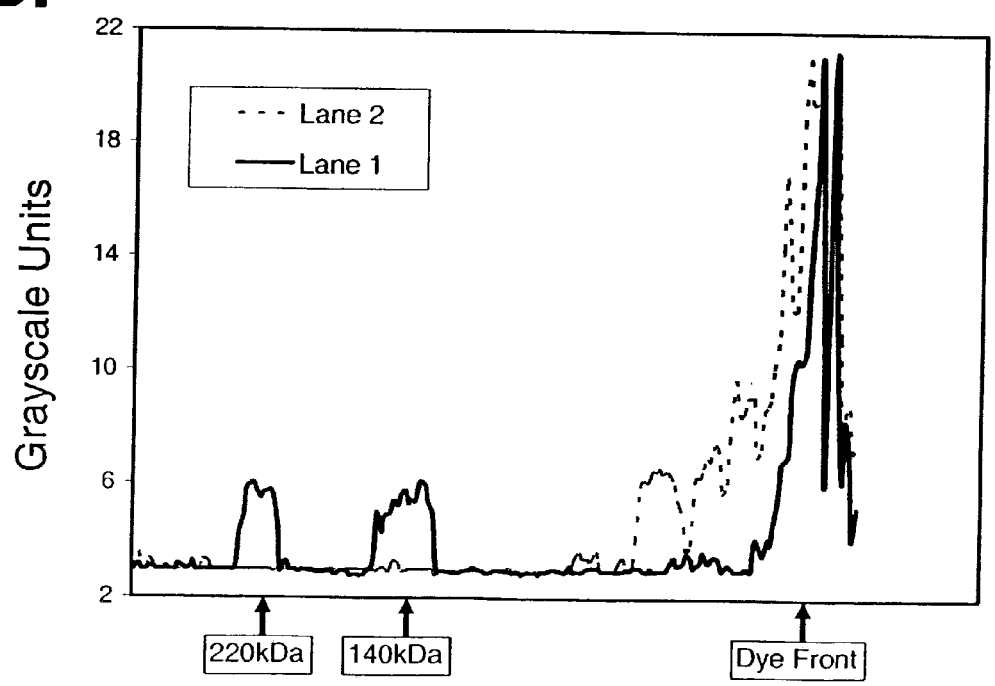

Figure 12
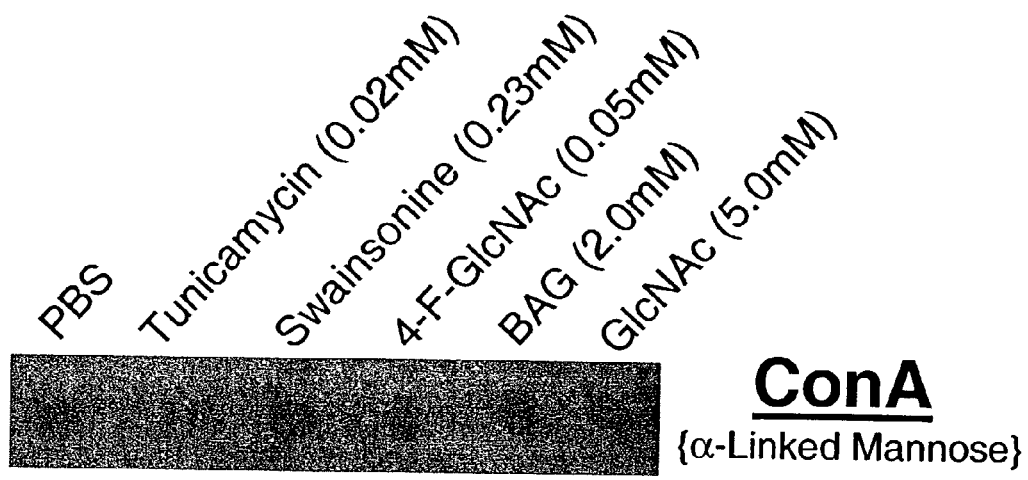
ConA
{α-Linked Mannose}
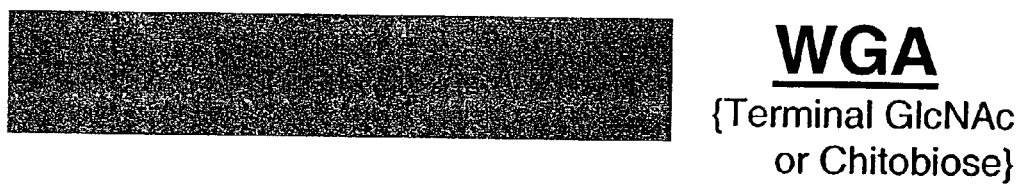
WGA
{Terminal GlcNAc or Chitobiose}
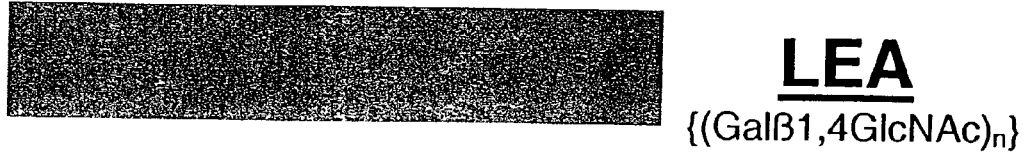
LEA
{(Galβ1,4GlcNAc)$_n$}

Figure 14
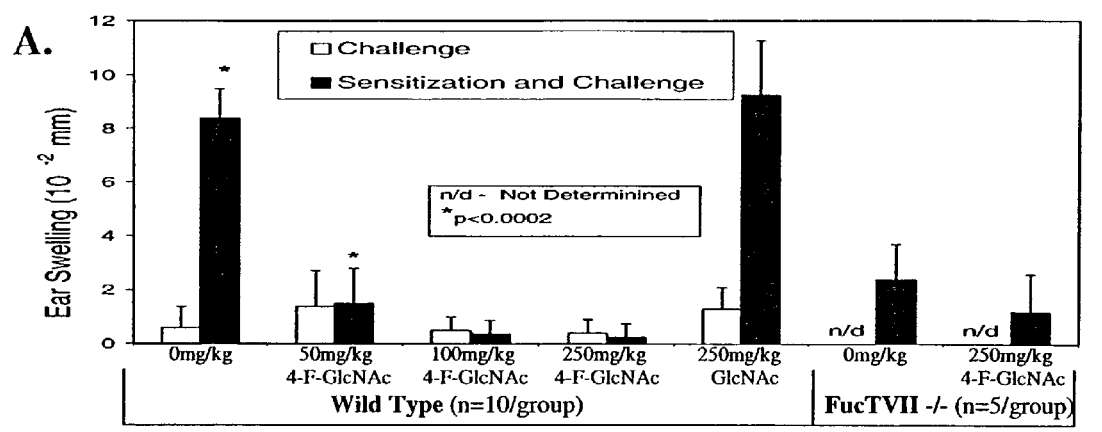
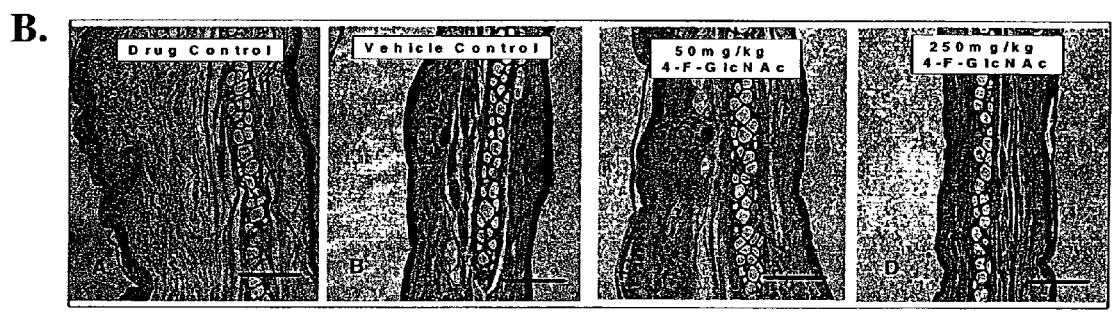

FLUORINATED GLUCOSAMINE ANALOGS USEFUL FOR MODULATING POST-TRANSLATIONAL GLYCOSYLATIONS ON CELLS

RELATED APPLICATIONS

This application claims priority to U.S. Ser. No. 60/334,151 filed, Nov. 28, 2001 which is incorporated herein by reference in its entirety.

STATEMENT AS TO FEDERALLY SPONSORED RESEARCH

This invention was made at least in part with funds received pursuant to Grant Nos. CA 84156 and HL 60528 from the National Institutes of Health, U.S. Department of Health and Human Services. Therefore, the U.S. Government has certain rights in the invention.

FIELD OF THE INVENTION

The invention relates to methods of producing fluorinated N-acetylglucosamines and their use in treating disease. More particularly, the invention relates to large scale synthesis of fluorinated N-acetylglucosamines and methods for modulating cellular migration and inflammation with fluorinated N-acetylglucosamines and providing for treatment of disorders associated therewith, including cancer, inflammatory diseases, hematologic diseases, perfusion and reperfusion injury, and contraception.

BACKGROUND OF THE INVENTION

The initial adhesive contacts between leukocytes and vascular endothelial cells are mediated by cell adhesion molecules called selectins. The selectin family of adhesion molecules mediate leukocyte tethering and rolling interactions on endothelial cells. Their expression on either the leukocyte (L-selectin) or endothelium (P- and E-selectin) helps the leukocyte "slow down" enabling cells in flow to respond to chemokine/cytokine signals, firmly attach and migrate through the endothelial lining into a tissue site. This primary intravascular braking mechanism is controlled by the $Ca^{++}$ dependent binding activity of the selectins directed against their respective ligands, which are comprised of carbohydrate determinants displayed on cell surface proteins or lipids expressed on leukocytes and/or endothelial cells. The cooperative involvement of all selectins and selectin ligands is critical for rapid and efficient recruitment of leukocytes at sites of inflammation. These molecular interactions are also necessary for the maintenance of steady state host immunity and tissue-specific homing as illustrated in lymphocyte homing to peripheral lymph nodes (L-selectin-mediated), trafficking of human memory T-cells to skin (E selectin-mediated), and human progenitor cell (HPC) entry into the bone marrow (BM) (E-selectin-mediated). The latter two paradigms represent physiologically relevant processes that are dependent, at least in part, on the cell adhesive interactions between vascular E-selectin, which is constitutively expressed on post-capillary venules in the skin and BM, and its leukocyte E-selectin ligands. The cell-specific expression of leukocyte E-selectin ligands is, therefore, an important feature in developing therapeutic strategies to selectively control the extent of leukocyte infiltration associated with the progression of skin or bone-marrow-related diseases.

Analogs of the naturally occurring cell surface carbohydrate N-acetylglucosamine (GlcNAc) have been synthesized that are fully-acetylated and possess an isosteric substitution of a fluorine for a hydroxyl group at the carbon 3- and 4-positions, 2-acetamido-2-deoxy-1,4,6-tri-O-acetyl-3-deoxy-3-fluoro-D-glucopyranose (3-F-GlcNAc) and 2-acetamido-2-deoxy-1,3,6-tri-O-acetyl-4-deoxy-4-fluoro-D-glucopyranose (4-F-GlcNAc) (Bernacki, R. J. et al. (1977) J. Supra. Stru., 7:235–250; Sharma, M. and W. Korvtnyk (1980) Carbohyd. Res., 79:39–51; Sharma, M. et al. (1990). Carbohyd. Res., 198:205–22):

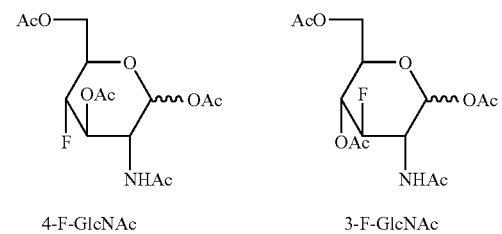

4-F-GlcNAc    3-F-GlcNAc

This structural modification has been postulated to cause the termination of poly-N-acetyllactosamine chain elongation or to inhibit the enzymatic processes of glycoconjugate metabolism involved in oligosaccharide biosynthesis (Bernacki, R. J. et al. (1977) J. Supra. Stru., 7:235–250). There is strong evidence that these compounds enter the cell by passive diffusion, rapidly de-O-acetylate and form UDP-fluorinated-N-acetylglucosamine, and incorporate into tumor cellular glycoproteins (Bernacki, R. J. et al. (1977) J. Supra. Stru., 7:235–250). Studies evaluating the effects of the fluorinated N-acetylglucosamine analogs 3-F-GlcNAc and 4-F-GlcNAc on human colon and ovarian cancer cell surface carbohydrate structure and glycoprotein function show that 3- or 4-F-GlcNAc treatment results in the selective termination of poly-N-acetyllactosamine chain formation and modulates the structure and function of tumor-associated glycoproteins (Woynarowska, B. et al. (1996) Glycoconjugate J., 13(4):663–674; Woynarowska, B. et al. (1994) J. Biol. Chem., 269(36):22797–22803). More specifically, treatment of human colon HT-29 cancer cells with 4-F-GlcNAc results in the inhibition of radiolabeled glucosamine, fucose and galactose incorporation into cell surface glycoproteins leading to quantitative reductions and qualitative structural changes in tumor-associated antigens: carcinoembryonic antigen (CEA), lysosomal-associated membrane proteins-1 and 2 (LAMPs) and sialyl Lewis antigen (Woynarowska, B. et al. (1994) J. Biol. Chem., 269(36):22797–22803). Similarly, 3- and/or 4-F-GlcNAc treatment of human ovarian, A121, tumor cells causes conspicuous reductions in the incorporation of radiolabeled sugar precursors and in the carbohydrate composition of LAMPs (Woynarowska, B. et al. (1996) Glycoconjugate J., 13(4):663–674). Preventing the glycosylation of CEA and LAMPs inhibits their capacity to function as homotypic and heterotypic adhesion molecules, respectively, and, therefore, reduces human colon and ovarian tumor cell adhesion and metastatic potential, in vivo (Woynarowska, B. et al. (1994) J. Biol. Chem., 269(36):22797–22803; Dimitroff, C. J. (1999) Thesis dissertation. SUNY (Buffalo Roswell Park Graduate School)).

SUMMARY OF THE INVENTION

The invention features methods of inhibiting cell migration, cell proliferation or cell differentiation by contacting a cell with a fluorinated N-acetylglucosamine (F-GlcNAc), e.g., 2-acetamido-2-deoxy-1,3,6-tri-O-acetyl-4-deoxy-4-fluoro-D-glucopyranose or 2-acetamido-2-deoxy-1,4,6-tri-O-acetyl-3-deoxy-3-fluoro-D-glucopyranose in an amount sufficient to inhibit cell migration, proliferation or differentiation.

Also provide by the invention is a method of decreasing an amount of HECA-452 epitope on a glycoprotein, e.g., PSGL-1 or CD44 on a cell, by contacting the cell with a fluorinated N-acetylglucosamine. The amount of the glycoprotein on the cell in the presence of the fluorinated N-acetylglucosamine as compared to in the absence of the fluorinated N-acetylglucosamine differs by less than 10%, 5% or 1%.

In another aspect the invention features a method of inhibiting inflammation in a tissue, e.g., dermal tissue of a subject by administering to the subject a fluorinated N-acetylglucosamine. The inflammation is for example, chronic inflammation, e.g., DTH, acute inflammation, cutaneous inflammation, psoriasis, inflammatory bowel disease, colitis or Crohn's disease. The fluorinated N-acetylglucosamine is administered prior to an inflammatory event. Alternatively, the fluorinated N-acetylglucosamine is administered after an inflammatory event. Administration is, intraperitoneal, subcutaneous, nasal, intravenous, oral, topical and transdermal delivery.

The cell is a leukocyte such as a lymphoid cell, e.g., T-cell or a hematopoietic cell. Alternatively, the cell is a cancerous cell such a leukemic cell or a lymphoma, e.g., cutaneneous lymphoma. The cell is further contacted with a chemotherapeutic agent such as daunorubicin (DNR), cytarabine (ara-C), idarubicin, thioguanine, etoposide, and mitoxantrone or an anti-inflammatory agent such as aspirin, ibuprofen, naproxen sodium, celecoxib, prednisone, prednisolone, and dexamethasone.

The invention provides an improved method for preparing fluorinated N-acetylglucosamine which comprises the intermediate step of preparing benzyl 2-acetamido-2-deoxy-3,6-di-O-benzyl-D-glucopyranoside from benzyl 2-acetamido-3-O-benzyl-4,6-benzylidene-2-deoxy-D-glucopyranoside, the improvement comprising (i) hydrolyzing benzyl 2-acetamido-3-O-benzyl-4,6-benzylidene-2-deoxy-D-glucopyranoside under appropriate conditions to form benzyl 2-acetamido-3-O-benzyl-2-deoxy-D-glucopyranoside; (ii) reacting benzyl 2-acetamido-3-O-benzyl-2-deoxy-D-glucopyranoside with a tin compound to form a tin complex comprising benzyl 2-acetamido-3-O-benzyl-2-deoxy-D-glucopyranoside; and (iii) reacting the tin complex with a benzylating agent under appropriate conditions to form benzyl 2-acetamido-3,6-benzyl-2-deoxy-D-glucopyranoside.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are hereby incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 5A is a schematic illustrating the structure of 2-Acetamido-1,3,6-tri-O-acetyl-4-fluoro-D-glucopyranose (4-F-GlcNAc). The carbons on the pyranose ring are indicated numerically starting with the anomeric carbon 1, which forms a glycosidic bond with the acceptor sugar in a β (up) or α (down) position.

FIG. 5B is a schematic illustrating the potential site of 4-F-GlcNAc incorporation into poly-N-acetyllactosamine chains. The large black arrows indicate the potential points of blockage or chain termination. Symbols: Fucose (Fuc), galactose (Gal), N-acetylneuraminic acid (NANA) and/or N-acetylglucosamine (GlcNAc).

FIG. 5C is a schematic illustrating the potential site of 4-F-GlcNAc incorporation into carbohydrate selectin-bindings determinants. The large black arrows indicate the potential points of blockage or chain termination. Symbols: Fucose (Fuc), galactose (Gal), N-acetylneuraminic acid (NANA) and/or N-acetylglucosamine (GlcNAc).

FIG. 6A is a photograph of a western blot showing CLA expression of human CLA T-cell cultures treated with neuraminidase then grown in the presence of diluent control (PBS), tunicamycin (0.02 mM), swainsonine (0.23 mM), 4-F-GlcNAc (0.05 mM), BAG (2.0 mM) or GlcNAc (5.0 mM, negative control) for 30 h.

FIG. 6C is a photograph of a western blot showing PSGL-1 expression of human CLA+T-cell cultures treated with neuraminidase then grown in the presence of diluent control (PBS), tunicamycin (0.02 mM), swainsonine (0.23 mM), 4-F-GlcNAc (0.05 mM), BAG (2.0 mM) or GlcNAc (5.0 mM, negative control) for 30 h.

FIG. 6C is a photograph of a western blot showing CD43 expression of human CLA T-cell cultures treated with neuraminidase then grown in the presence of diluent control (PBS), tunicamycin (0.02 mM), swainsonine (0.23 mM), 4-F-GlcNAc (0.05 mM), BAG (2.0 mM) or GlcNAc (5.0 mM, negative control) for 30 h.

FIG. 9A is a table showing the expression of HECA-452 epitopes and PSGL-1 after bromelain treatment.

FIG. 9B is a photograph of a western blot from human CLA+ T-cell cultures treated with bromelain.

FIG. 9C is a photograph of a western blot from human CLA+ T-cell cultures treated with bromelain.

FIG. 11A is a photograph of a autoradiograph of PSGL-1 immunoprecipitated from human CLA+ T-cells metabolically radiolabeled with 4-F-Glc[³H]NAc.

FIG. 11B is a schematic illustrating comparative densitometric scans of lanes 1 and 2 in FIG. 11A using NIH ImageJ software confirmed the appearance of 220 and 140 kDa forms of PSGL-1 immunoprecipitated from radiolabeled lysate.

FIG. 12 is a photograph showing lectin blot analysis of glycoconjugates isolated from human CLA+ T-cells treated with glycosylation inhibitors.

FIG. 14A is a bar chart showing anti-inflammatory effects of 4-F-GlcNAC in vivo.

FIG. 14B are photographs of histological analysis illustrating cutaneous delayed type conatact hypersensitivity in mice treated with 4-F-GlcNAC.

DETAILED DESCRIPTION OF THE INVENTION

Figure 1:
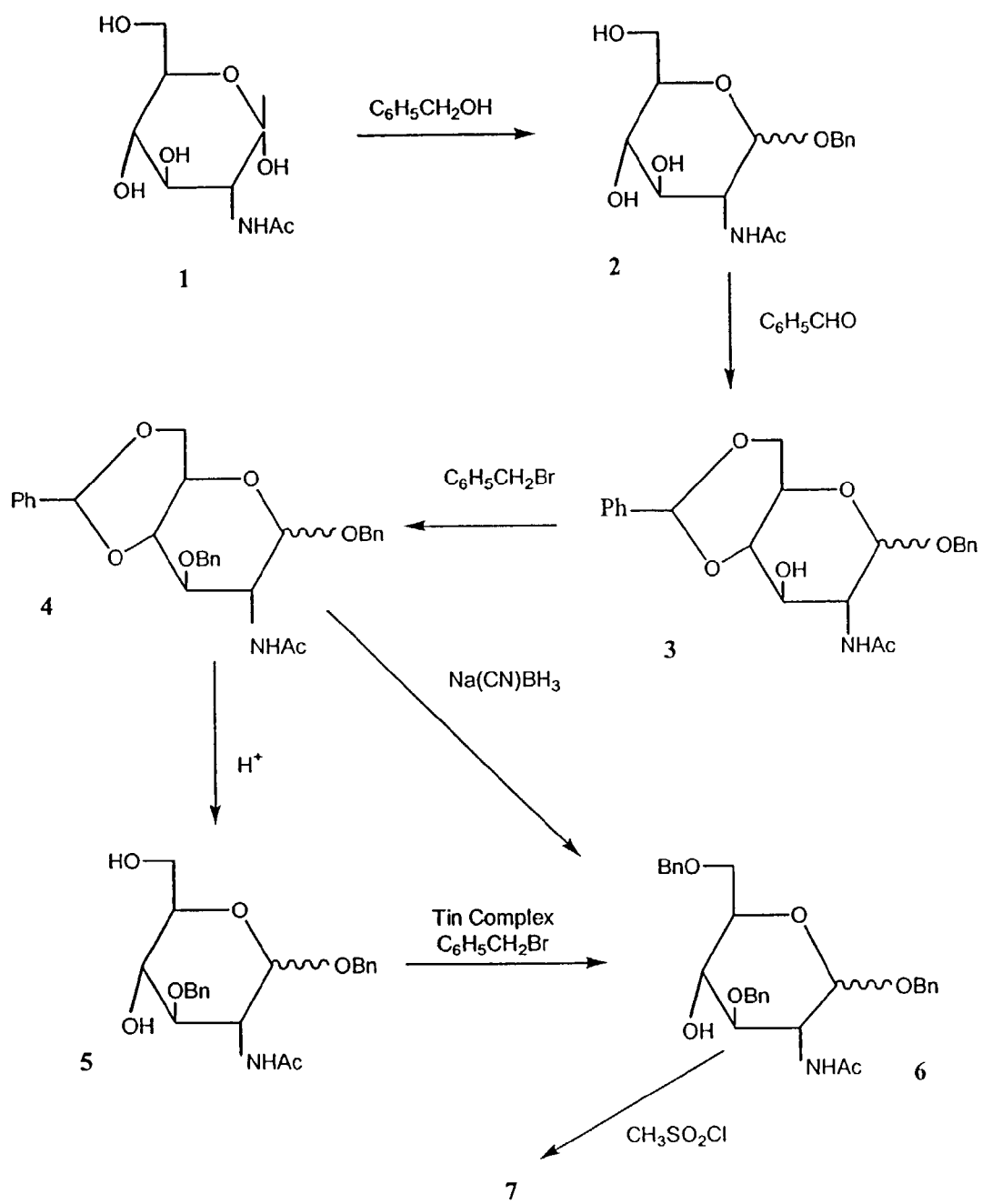
FIG. 1 is a schematic illustrating a preferred embodiment for the method of producing 3- and 4-F-GlcNAc according to the invention.

The invention is based in part on the discovery that a fluorinate analog of N-acetylglucosamine alters HECA-452 epitope expression on human CLA+ T-cells and inhibits selectin binding under shear stress. The fluorinated N-acetylglucosamine was directly incorporated into native CLA expressed on T-cells, indicating direct inhibition on poly-N-acetyllactosamine elongation and selectin-binding determinants on PSGL-1 O-glycans.

Tissue-specific migration of lymphocytes to skin is critical to the pathobiology of cutaneous graft versus host disease (GVHD), of neoplastic conditions (e.g. lymphoma cutis, mycosis fungoides), and of inflammatory skin diseases (e.g. psoriasis, atopic/allergic dermatititis). Cutaneous lymphocyte-associated antigen (CLA) is a sialyl Lewis X-like carbohydrate epitope recognized by the rat monoclonal antibody HECA452 that is displayed on the sialomucin-like molecule, P-selectin glycoprotein ligand-1 (PSGL-1). CLA engages in binding interactions with P-selectin and functions as the primary E-selectin ligand on skin-homing T-cells. The expression of HECA 542 reactive PSGL-1 (i.e., CLA), on normal human lymphocytes and malignant leukocytes directly correlates with the functional capacity of these cells to enter skin (1–10). Though CLA is expressed on a subset of primitive human hematopoietic progenitor cells (35–38) as well as on dendritic cells, monocytes and neutrophils (12), CLA expression is conspicuously up-regulated on effector lymphocytes and on malignant cells in patients with cutaneous inflammatory disease, leukemia and lymphoma (1, 5–10, 14, 47–50). Targeting the expression of CLA and more specifically HECA-452 epitopes offers a therapeutic approach for modulating leukocyte migration to skin, as HECA-452 reactivity and not PSGL-1 polypeptide itself, confers the specificity if human T-cell to enter dermal tissue.

In its various aspects the invention provides methods of inhibiting cell migration, cell proliferation or cell differentiation by contacting a cell with a fluorinated N-acetylglucosamine (F-GlcNAc) in an amount sufficient to inhibit cell migration, proliferation or differentiation.

The invention further provides a method of decreasing HECA-452 epitope on a glycoprotein on a cell by contacting the cell with a fluorinated N-acetylglucosamine. Preferably, treatment of the cell with the F-GlcNAc does not effect expression of the glycoprotein on the cell surface. More preferably, treatment does not effect expression of other carbohydrate structures on the glycoprotein. For example, the amount of glycoprotein on the cell in the presence of F-GlcNAc as compared to the absence of F-GlcNAc differs by less than 10%, 5% or 1%.

HECA-452 epitope expression is measured for example by reactivity with an antibody that recognizes the HECA-452 epitope such monoclonal antibody HECA-452. (ATCC Number: HB-11485). Alternatively, HECA-452 expression is measured by determining they ability of the cell to bind selectins, (i.e., E-, P-, or L-selectin). The glycoprotein is any protein capable of expressing the HECA-452 epitope, for example the protein is PSGL-1 or CD44.

The invention further provides methods if inhibiting inflammation of a tissue in a subject by administering to a subject in need thereof a fluorinated N-acetylglucosamine such that inflammation is inhibited. The subject is further administered an anti-inflammatory compound. The tissue is dermal, respiratory or gastrointestinal. The subject suffers from or is at risk of developing an inflammatory disorder. Administration is prophylactic (i.e., administered before an inflammatory event). Alternatively, the administration is therapeutic (i.e., after an inflammatory event).

A subject suffering from or at risk of an inflammatory disorder is determined by standard diagnostic techniques know in the art to be associated with the particular disorder, for example, rectal bleeding, intestinal pain, nausea, vomiting, itchy plaque-like lesions on the skin, redness or soreness of the skin, blood test, allergies, or family history. Inflammatory disorders include, chronic inflammatory disorders or acute inflammatory disorders. Inflammatory disorders include, but are not limited to, delayed type hypersensitivity (DTH) graft versus host disease(GVHD), psoriasis, asthma, inflammatory bowel disease, colitis, (e.g., ulcerative colitis) and Crohn's diseases.

The cell population that is exposed to, i.e., contacted with, F-GlcNAc can be any number of cells, i.e., one or more cells, and can be provided in vitro, in vivo, or ex vivo. For example, the cell is contacted with the F-GlcNAc at an effective local concentration of between 0.01 mM and 100 mM. Preferably, the concentration is between 0.01 mM and 25 mM. More preferably, the concentration is between 0.01 and 10 mM. Most preferably, the concentration is between 0.05 and 5 mM.

Exemplary fluorinated N-acetylglucosamines include 2-acetamido-2-deoxy-1,3,6-tri-O-acetyl-4-deoxy-4-fluoro- D-glucopyranose and 2-acetamido-2-deoxy-1,4,6-tri-O-acetyl-3-deoxy-3-fluoro-D-glucopyranose.

The cell is any cell which expresses the HECA-452 epitope. For example the cell is a leukocyte, e.g., myeloid, lymphoid, reticular or a prostate cell. Leukocytes include, lymphocytes, monocytes, macrophages, langerhans cells, dendritic cells, granulocytes, plasmacytes, hematopoietic cells, such as a hematopoietic stem cell or any cell that is capable of becoming a leukocyte. The lymphocyte is a B-cell or a T-cell such as a Th1 cell. The cell is a normal (i.e., non-cancerous) cell. Alternatively, the cell is a cancerous. The cancer cell is a primary tumor such as a cell derived from a subject with cancer. Alternatively, the cancer cell is derived from a metastatic lesion from a subject with cancer. The cancer cell is any cell type, e.g., epithelial, germ cell, squamous, myeloid, or lymphoid. For example, the cell is a leukemia cell, or a lymphoma such as cutaneous lymphoma.

The cell can be further contacted with a chemotherapeutic compound or anti-inflammatory compound. The chemotherapeutic compound is, for example, paclitaxel, taxol, lovastatin, minosine, tamoxifen, gemcitabine, 5-fluorouracil (5-FU), methotrexate (MTX), docetaxel, vincristin, vinblastin, nocodazole, teniposide, etoposide, adriamycin, epothilone, navelbine, camptothecin, daunonibicin, dactinomycin, mitoxantrone, amsacrine, thioguanine, cytarabine, epirubicin or idarubicin. The anti-inflammatory compound includes for example, a non-steroidal anti-inflammatory drug such as aspirin (Bayer, Bufferin), ibuprofen (Motrin, Advil), naproxen sodium (Aleve), ketoprofen (Orudis KT), indomethacin (Indocin), etodolac (Lodine), diclofenac sodium (Voltaren), rofecoxib (Vioxx), celecoxib (Celebrex), nabumetone (Relafen) or a steroid such as prednisone, prednisolone, dexamethasone, beclomethasone, budesonide, fluticasone or triamcinolone.

By cell migration is meant movement of cell from on location to another. Migration is in vitro, alternatively migration is in vivo. Migration is measured, for example, by counting cell migration out of a defined area in a tissue culture over time. For example a micro-chemotaxis chamber or a Boyden chamber is used.

By cell proliferation is meant the cells are dividing (i.e., reproducing). Cell proliferation is measured for example using a clonogenic assay. Clonogenic assay are known to those skilled in the art. Alternatively, cell proliferation is determined by measuring DNA synthesis (i.e., $^3$H thymidine or bromodeoxyuridine)

By cell differentiation is meant the development of a cell of one type to that of another cell type such as the process of cell maturation from pluripotent cell (e.g., stem cell or progenitor cell) to unipotent cell or process of a normal cell becoming a tumor cell. An example of differentiation in humans is hematopoiesis in which pluripotent stem cells (in the bone marrow) divide and differentiate, passing through many recognizable intermediate steps to form red blood cells, platelets, white blood cell. Malignant cells can arise at any stage during the process of differentiation, leading to many different types of leukemia's.

Modulation of cellular migration provides methods of prophylaxis and treatment for conditions and diseases including, but not limited to, acute and chronic inflammation, sepsis, autoimmune disorders, arthritis, hematologic diseases, cancers, perfusion-reperfusion injury, and also provides for methods of contraception. In preferred embodiments, disorders linked to leukocyte interaction with endothelial cells include, but are not limited to, acute and chronic inflammation, autoimmune disorders, tumor metastasis, infectious diseases, and leukocyte-associated skin disorders such as cutaneous T-cell lymphoma, atopic/allergic dermatitis, graft vs. host disease, psoriasis, and mycosis fungoides. In a particularly preferred embodiment of the method of treating disorders associated with hematopoietic cells with bone marrow, the hematopoietic cells are malignant. Thus, the invention provides, for example, for methods of treating cancer cell growth and/or malignancy, treating perfusion-reperfusion injury, and methods of contraception by administration of fluorinated N-acetylglucosamine to a subject in need thereof.

As practiced in vivo the fluorinated N-acetylglucosamine is administered to a subject in need of prophylaxis, treatment or therapy in doses at which an appropriate prophylactic or therapeutic effect is demonstrated, and preferably at a dosage of between about 1 mg/kg to about 500 mg/kg. Preferably ,a dosage of between about 25 mg/kg–250 mg/kg. Most preferably, a dosage less than 50 mg/kg. Essentially, any disorder in a subject which is etiologically linked to carbohydrate-dependent cell-cell interaction, specifically the HECA-452 epitope is subject to treatment by the methods of the invention.

The subject is preferably a mammal. The mammal can be, e.g., a human, non-human primate, mouse, rat, dog, cat, horse, or cow.

Methods for Preparing Fluorinated N-acetylglucosamines.

Methods of preparing fluorinated N-actetylglucosaimes are known in the art. The preferred embodiment of the active components of the pharmaceutical compounds of the invention, i.e., fully acetylated 3-fluoro- or 4-fluoro-N-acetyl-D-glucosamine (3-F-GlcNAc or 4-F-GlcNAc), can be prepared as described in Sharma et al., *Carbohydrate Research* (1990) Vol. 198 pp. 205–221, and in Thomas et al., *Carbohydrate Research* (1988) Vo. 175, pp. 153–157, the contents of which are hereby incorporated by reference in their entirety. The method of Sharma et al. and Thomas et al. is fully enabling for preparation of the compounds on the scale described therein. However, it was discovered by the inventors that when preparing larger lots, the reductive cleavage of benzyl 2-acetamido-3-O-benzyl-4,6-O-benzylidene-2-deoxy-D-glucopyranoside to form benzyl 2-acetamido-3,6-dibenzyl-2-deoxy-D-glucopyranoside by treatment with sodium cyanoborohydride did not provide the desired product. Therefore, an alternative, preferred procedure was developed whereby the 4,6-O-benzylidene was hydrolyzed with acid such as acetic acid to form benzyl 2-acetamido-3-O-benzyl-2-deoxyl-D-glucopyranoside. The hydrolyzed product was then converted to its tin complex by reaction with bis(tributyltin)oxide in toluene then treated with benzyl bromide to form the desired benzyl 2-acetamido-2-deoxy-3,6-di-O-benzyl-D-glucopyranoside.

Figure 2:
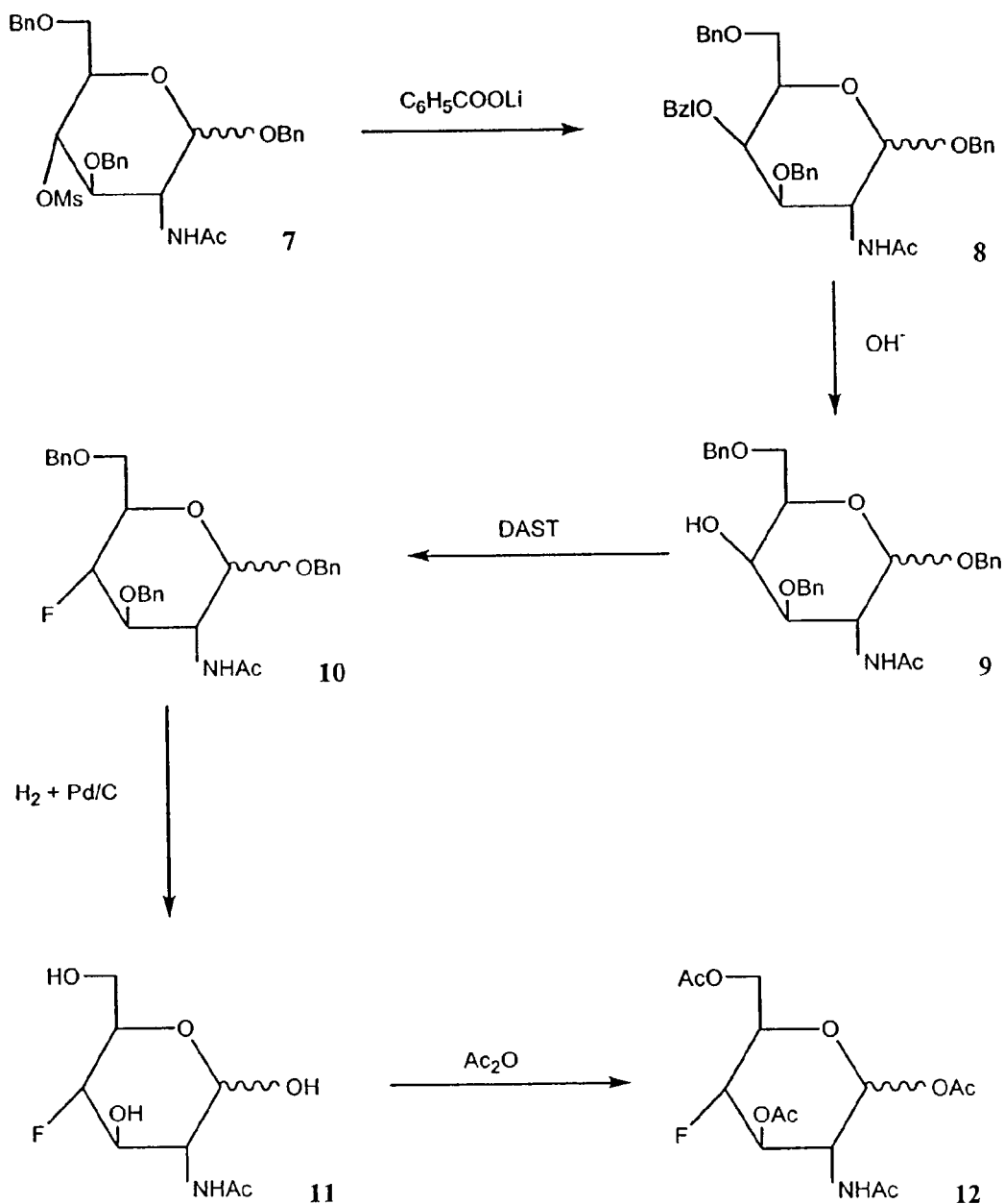
FIG. 2 is a schematic illustrating illustrate a preferred embodiment for the method of producing 3- and 4-F-GlcNAc according to the invention.

Thus, in a preferred method, the compounds may be prepared using the following method, which allows for easier scale up for preparing larger amounts of the active components. In this process, as described in FIGS. 1 and 2, the starting material, N-acetyl-D-glucosamine 1, is converted to benzyl 2-acetamido-2-deoxy-D-gucopyranoside 2 by treatment with benzyl alcohol in the presence of acid such as HCl. The reaction is carried out at elevated temperature for a period of 5 to 7, preferably 6 hours, then reacted at room temperature for a period of about 18 hours, followed by addition of ether and reaction for an additional 72 hours. The benzyl glycopyranoside product 2 can be recovered from ethanol/ether and dried. The benzyl glycopyranoside product 2 is then reacted with benzylaldehyde over zinc catalyst to give benzyl 2-acetamido-4,6-O-benzylidene-2-deoxy-D-glucopyranoside 3. The reaction is generally carried out at room temperature for approximately 1–3 days with addition of pet ether, ethanol and water and then stored on ice for several days. The precipitate can then be recovered from ethanol and ether. The benzylidene derivative 3 is next reacted with benzyl bromide to give benzyl 2-acetamido-3-O-benzyl-4,6-benzylidene-2-deoxy-D-glucopyranoside 4. The reaction is carried out in the presence of barium oxide and barium hydroxide at room temperature for several days then cooled in an ice bath and pH lowered to slightly acidic level. The product can be recovered from trichloromethane and dried to produce the 4,6-benzylidene 4. The 4,6-benzylidene product can then be hydrolyzed for example with acetic acid at elevated temperature for a period of 2–3 hours and crystallized from methanol/ether and dried to produce benzyl 2-acetamido-3-O-benzyl-2-deoxyl-D-glucopyranoside 5.

The hydrolyzed product is then converted to benzyl 2-acetamido-2-deoxy-3,6-di-O-benzyl-D-glucopyranoside 6 by treating its tin complex with benzyl bromide. The tin complex can be formed by reacting the hydrolyzed product with bis(tributyltin)oxide in toluene for about approximately 0.5 to 1.5 hr, preferably 1 hr, after which t-butyl ammonium bromide and benzyl bromide are added and allowed to react at elevated temperature for 1–3, preferably 2 days. The reaction is quenched by cooling, diluted with methylene chloride, washed with saturated sodium carbonate solution, with water, then dried over anhydrous sodium sulfate. The 4-O-methanesulfonyl derivative 7 can then be prepared by adding mesyl chloride drop wise to a solution of 6 in pyridine, stirring on ice for approximately 1 day. The product can be recovered as a precipitate from ice water, washed with water and methylene chloride and dried over sodium sulfate. The 4-O-methanesulfonyl derivative is then converted to the 4-O-benzoyl galacto derivative 8 by reaction with lithium benzoate at reflux for approximately 12 to 24, preferably 18, hours. The reaction is cooled and quenched in ice water, to which organic solvent such as methylene chloride is added. The product 8 is obtained from the organic fraction, washed and then dried over sodium sulfate. The benzoyl group on 8 can then be hydrolyzed to form 9 by reacting with methanol and sodium metal over an ice bath. The 4-hydroxy galacto product 9 is obtained by partitioning between methylene chloride and water and dried over anhydrous sodium sulfate. The 4-hydroxy galacto product 9 can be converted to the 4-fluoro gluco compound 10 by adding a methylene chloride solution of 9 dropwise to a chilled methylene chloride solution of N,N-diethylaminosulfurtrifluoride (DAST) and then stirring with added anhydrous pyridine. The product 10 is obtained by partitioning between methylene chloride and water and dried over anhydrous sodium sulfate.

The benzyl protecting groups on 10 can be removed by hydrogenation in the presence of Pd/C catalyst, such as 10% Pd/charcoal, typically at approximately 50–55 psig for a period of about 1–5 days. The resulting 2-acetamido-2,4-dideoxy-4-fluoro-D-glucopyranose 11 can then be acetylated by treatment with acetic anhydride in pyridine for a period of 1 to 2 days, to give the desired fully acetylated 4-fluoro-N-acetylglucosamine.

Purified products from each of the reaction steps are typically obtained by chromatography such as by elution on silica gel. Although the above reaction demonstrates production of the 4-fluoro-derivative, those of ordinary skill in the art will recognize that slight modification by routine means will readily produce the 3-fluoro-derivative.

Thus, this invention provides an improved method for preparing fluorinated N-acetylglucosamine wherein the intermediate step of preparing benzyl acetamido-2-deoxy-3,6-di-O-benzyl-2-deoxy-D-glucopyranoside from benzyl 2-acetamido-3-O-benzyl-4,6-benzylidene-2-deoxy-D-glucopyranoside, is accomplished by (i) hydrolyzing benzyl 2-acetamido-3-O-benzyl-4,6-benzylidene-2-deoxy-D-glucopyranoside under appropriate conditions to form benzyl 2-acetamido-3-O-benzyl-2-deoxy-D-glucopyranoside; (ii) reacting benzyl 2-acetamido-3-O-benzyl-2-deoxy-D-glucopyranoside with a tin compound to form a tin complex comprising benzyl 2-acetamido-3-O-benzyl-2-deoxy-D-glucopyranoside; and (iii) reacting the tin complex with a benzylating agent under appropriate conditions to form benzyl 2-acetamido-3-O-benzyl-3,6-di-O-benzyl-2-deoxy-D-glucopyranoside.

In separately preferred embodiments of the method, the tin compound is bis(tributyltin)oxide, and the benzylating agent is benzyl bromide.

The invention thus also provides a method of making a compound having the formula (I):

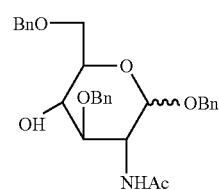

I which comprises reacting N-acetyl-D-glucosamine with a benzylating agent under appropriate conditions to produce a compound having the formula (II):

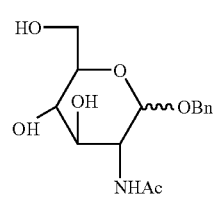

II reacting the compound (II) with a benzaldehyde under appropriate conditions to produce a compound having the formula (III):

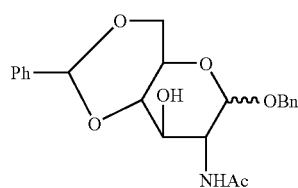

III reacting the compound (III) with a benzylating agent under appropriate conditions to produce a compound having the formula (IV):

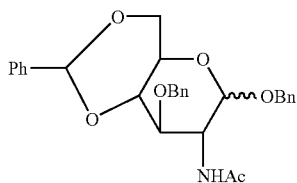

reacting compound (IV) with a hydrolyzing agent under appropriate conditions to produce a compound having the formula (V):

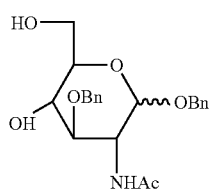

reacting compound (V) with a tin compound to produce a tin complex comprising compound (V) and reacting the tin complex with a benzylating agent under appropriate conditions to produce compound (I).

Pharmaceutical Compositions Including Flourinated Glucosamine Analogs.

The fluorinated glucosamine analogs 3- and 4-F-GlcNAc, (also referred to herein as "Therapeutics" or "active compounds") of the invention, and pharmaceutically acceptable derivatives or salts thereof, can be incorporated into pharmaceutical compositions suitable for administration. Such compositions typically comprise the active compound and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The active compounds disclosed herein can also be formulated as liposomes. Liposomes are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter.

A pharmaceutical composition of the invention is formulated to be compatible with its intended route of administration. Examples of routes of administration include parenteral (e.g., intravenous), intradermal, subcutaneous, oral, respiratory, (e.g., inhalation), transdermal (i.e., topical), transmucosal, and vaginal or rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., 3-F-GlcNAc or 4-F-GlcNAc) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery and in the form of suppositories, gels or sponges for vaginal delivery. For example, the compounds can be incorporated into devices for administration vaginally, such as incorporation into a sponge as described in U.S. Pat. No. 5,527,534, or a dissolvable vehicle as described in U.S. Pat. No. 5,529,782.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In some embodiments, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Sustained-release preparations can be prepared, if desired. Suitable examples of sustained-release preparations include semipermeable matrices of solid hydrophobic polymers containing the active compound, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The pharmaceutical compositions can be included in a container, pack, or dispenser together with instructions for administration.

Those of ordinary skill in the art are well versed in determining the amounts of therapeutic compound to be administered in the practice of the methods of the invention. Such factors to consider about the subject to be treated, including sex, weight, type and extent of disorder, are typically analyzed in order to determine the correct dosage for treating the disorder. In a preferred embodiment for treating humans suffering from a disorder as defined above, the dosages are typically in the range of about 4 mg/kg to about 50 mg/kg.

EXAMPLES

Example 1

Benzyl 2-acetamido-2-deoxy-D-glucoyranoside

To vigorously stirred benzyl alcohol (2.5 L) (Aldrich) was added a strong stream of anhydrous HCl gas for 5 min. (initial temperature rose to approx. 50°). To this solution was added 2-acetamido-D-glucose (400 g, 1.808 mol) (Sigma). This mixture was then stirred at 70°±2° for 6 hours then stirred at room temperature for 18 hours. Diethyl ether (5.5 L) was then added, in portions, over 8 hours. The reaction mixture was then stored at room temperature for 72 hours with stirring, during which time more ether was added for a total of 8.0 L. The pink suspension was then stirred at room temperature for an additional 18 hours. The product was collected, in portions, on 2 coarse glass frit filter funnels. Each portion was washed with ether-pet ether (1:1) then combined in a suspension with absolute EtOH (3.0 L). This suspension was boiled until homogenous, then set aside to evaporate slowly. The crystalline suspension was now stored at 0° for several days. The product was then collected on a coarse glass frit, drained thoroughly, washed in situ with cold absolute EtOH (2×200 ml), then dried in vacuo at room temperature over $P_2O_5$ to a constant weight. Yield=326.32 g (58.0%).

Example 2

Benzyl 2-acetamido-4,6-O-benzylidene-2-deoxy-D-glucopyranoside

To a well-stirred mixture of zinc chloride (167 g, 1.23 mol) in dry benzaldehyde (550 ml) was added benzyl 2-acetamido-2-deoxy-D-glucopyranoside (166.542 g, 0.5348 mol). This mixture was stirred at room temperature for 20 hours, then stirred at 40°±3° for 4 hours to dissolve a small amount of remaining solid, then stirred at room temperature for 18 hours. The well-stirred reaction solution was now diluted with pet. ether (1000 ml), absolute EtOH (250 ml) and $H_2O$ (400 ml). The reaction mixture was stirred for 2 days at room temperature, then stored at 0° for 11 days. The curdy white precipitate was collected on a coarse glass frit funnel, drained thoroughly, then washed by re-suspension in absolute EtOH (approx. 500 ml). The white finely divided solid was drained thoroughly, re-suspended in diethyl ether (approx. 500 ml), re-drained thoroughly, and then dried in vacuo at room temperature over $P_2O_5$. Yield=139.76 g (65.4% dry; 62.6% as hydrate).

Example 3

Benzyl 2-acetamido-3-O-benzyl-4,6-O-benzylidene-2-deoxy-D-glucopyranoside

A well-stirred solution of barium oxide (153.97 g, 1.004 mol), barium hydroxide (anhydrous; 320 g, 1.87 mol) and benzyl bromide (147 ml, 1.23 mol) (Aldrich) in dry DMF (200 ml) was cooled to 0–5°, when benzyl 2-acetamido-4,6-O-benzylidene-2-deoxy-D-glucopyranoside (179.74 g, 0.4500 mol) was added. This suspension was stirred at room temperature for 6 days, then cooled in an ice water bath while 10% aqueous formic acid was added, drop-wise, to pH of 5–6 (approx. 1350 ml required). The heavy white solid product was then collected on coarse glass fritted funnels, drained, then washed with $H_2O$ (4×500 ml). The well drained white solid was then dried in vacuo at room temperature over $P_2O_5$ to a constant weight. Crude yield=262.21 g (100+%). The crude product was triturated in boiling $CHCl_3$ (3000 ml) and insoluble material was removed by filtration. A white solid precipitated from the filtrate was again suspended in $CHCl_3$ (3000 ml). The first white precipitate was collected on a filter, washed with a small amount of $CHCl_3$ then dried in vacuo at room temperature over $P_2O_5$ to yield final product. The filtrate from this material was evaporated to a dry residue to yield additional product. Total yield=174.13 g (79.1%).

Example 4

Benzyl 2-acetamido-3-O-benzyl-2-deoxy-α-D-glucopyranose

A stirred suspension of benzyl 2-acetamido-3-O-benzyl-4,6-O-benzylidene-2-deoxy-α-D-glucopyranose (101.92 g, 0.2082 mol) in 60% aqueous HOAc (2100 ml) (J T Baker) was warmed to form a solution then heated at reflux for 2.5 hours. Solvent was removed by evaporating in vacuo to give a solid residue, which was co-evaporated with $H_2O$ (3×150 ml). The solid residue was dried in vacuo for approximately 3 hrs. then triturated in hot pet. ether (approx. 1000 ml). The insoluble material was collected on a filter then washed with a little pet. ether. The insoluable material was dissolved in methanol then re-evaporated to a solid, which was dried in vacuo for 18 hours. This material was then dissolved in hot methanol (200 ml) and ether (approx. 250 ml) was added to initiate crystallization. More ether was added occasionally to the cold suspension to further crystallization. Finally, the thick suspension was filtered to collect the solid product, which was washed with several serial portions of ether. This material was then dried in vacuo at room temperature over $P_2O_5$. Yield=35.03 g (41.9%).

Example 5

Benzyl 2-acetamido-2 deoxy-3,6-di-O-benzyl-α-D-glucopyranoside

A suspension of benzyl2-acetamido-3-O-benzyl-2-deoxy-α-D-glucopyranoside (43.24 g, 0.1077 mol) in toluene (2200 ml) was refluxed under a moisture trap for one hour, during which time approximately 25 ml of wet solvent was removed. The suspension was cooled and bis(tributyltin) oxide (Aldrich) (46 ml, 0.090 mol) was added. The reaction solution was again refluxed under a moisture trap, which was periodically emptied. After 24 hours, approximately 250 ml of wet toluene was removed. The reaction was cooled to approximately 75°; then tetrabutyl ammonium bromide (17.8 g, 0.0552 mol) and benzylbromide (43 ml, 0.36 ml) were added. The reaction solution was stirred at 80° for 24 hrs., when a small sample was withdrawn & checked via TLC. The product appeared, but much starting material remained. Therefore, tetrabutyl ammonium bromide (17.9 g, 0.0555 mol) and benzylbromide (43 ml, 0.36 mol) was added, and the reaction solution was again stirred at 80° for 24 hours. A sample was again withdrawn and checked by TLC. Some starting material remained, so stirring at 80° was continued an additional 48 hours for a total of 96 hours at which time TLC showed no starting material. The reaction solution was then cooled to 35°, diluted with $CH_2Cl_2$ (1200 ml), and washed with saturated $NaHCO_3$ (300 ml) followed by $H_2O$ (3×300 ml). After drying over $Na_2SO_4$, solvent was removed by evaporating in vacuo to give a yellow oil. Crude yield=192.82 g.

TLC showed product, with front-running benzylbromide. A 750 g (approx. 1800 ml) column of silica gel was poured in $CH_2Cl_2$. The oily product was adhered to 150 g of silica gel then added to the column. The column was then eluted with $CH_2Cl_2$. The first material removed from the column was benzylbromide, which was discarded. The second fraction contained product contaminated with benzylbromide and a fast-running impurity. The next material to elute was virtually pure product, which was dried in vacuo at room temperature after removal of solvent by evaporation in vacuo. This fraction was thoroughly triturated in petroleum ether (200 ml). The resulting solid was collected on a filter then washed with several small portions of petroleum ether and dried in vacuo for 15 hours. Further elution of the column with $CH_2Cl_2$ produced further product which was dried in vacuo at room temperature. Total crude yield=54.48 g (100+%).

Example 6

Benzyl 2-acetamido-3,6-di-O-benzyl-2-deoxy-4-O-mesyl-α-D-glucopyranoside

To a stirred solution of benzyl2-acetamido-3,6-di-O-benzyl-2-deoxy-α-D-glucopyranose (37.4 g, 0.076 mol) in pyridine (400 ml), cooled in an ice-water bath, was added, dropwise, mesyl chloride (Aldrich) (25ml, 0.32 mol), over 45 min. The resulting dark mixture was stirred at 0° for 24 hours, until TLC showed no more starting material remained. The reaction mixture was poured into ice-water (1000 ml) and the resulting suspension was stirred for approximately 3 hours. The precipitated solid was collected on a filter, washed several times with small portions of $H_2O$, then taken up in $CH_2Cl_2$ (approx. 500 ml). This solution was washed with $H_2O$ (3×200 ml) then dried over arhydrous $Na_2SO_4$. The aqueous filtrate from above, on stirring for 3 days, again deposited a solid. This material was collected on a filter, taken up in $CH_2Cl_2$ (approx. 250 ml), then the solution was washed with $H_2O$ (3×250 ml). After drying over anhydrous $Na_2SO_4$, the combined extracts were evaporated in vacuo to a very dark red residue, which was dried in vacuo for several hours. Yield=41.38 g (96.0%).

This material was then dissolved in warm $CH_2Cl_2$ (150 ml) and an approximately equal amount of ether was added. The suspension was set aside to crystallize at 0° for 18 hours. The crystallized product was collected on a filter, washed with several small portions of ether, then dried in vacuo at room temperature over $P_2O_5$ for 18 hours. The filtrate was then evaporated in vacuo to a residue, which was dried briefly. This material was found to contain mostly product and base-line materials. Accordingly, this material was adhered to silica gel (20 g), then placed on a 200 g silica gel column (600 ml). The column was eluted with $CH_2Cl_2$. The first material off the column was a dark red oil which was discarded. The product eluted next, along with a pale yellow impurity. Total Yield=34.17 g (79.3%).

Example 7

Benzyl 2-acetamido-4-O-benzoyl-3,6-di-O-benzyl-2-deoxy-α-D-galacto pyranoside

A stirred solution of benzyl2-acetamido-3,6 di-O-benzyl-2-deoxy-4-O-mesyl-α-D-glucopyranose (44.07 g, 0.07736 mole) and lithium benzoate (Aldrich) (235 g, 1.84 mol) in dry DMF (800 ml) was heated at reflux for 48 hours, cooled to room temperature, then poured into ice water (3200 ml). This suspension was stirred for one hour; then $CH_2Cl_2$ (500 ml) was added and the 2-phase mixture was stirred at room temperature for 18 hours. The aqueous layer was separated then extracted with $CH_2Cl_2$ (3×500 ml). The combined organic extracts were washed with $H_2O$ (3×500 ml) then dried over anhydrous $Na_2SO_4$. Solvent was evaporated in vacuo to give a brown oil which was dried briefly in vacuo. A TLC of the crude product showed that only a small amount of mesyl starting material that was not converted to benzoyl. A 600 g silica gel column was poured in $CH_2Cl_2$ (75×330 mm, 1460 ml). To the crude product was added 60 g of Silica gel and $CH_2Cl_2$, to adhere the crude oil. This was added to the column and then eluted with $CH_2Cl_2$. Fractions containing the leading spot were pooled then evaporated in vacuo to an amber oil, which was dried. Yield=35.38 g (76.8%).

Example 8

Benzyl 2-acetamido-3,6-di-O-benzyl-2-deoxy-α-D-galactopyranoside

To a stirred solution of benzyl2 acetamido-4-O-benzoyl-3,6-di-O-benzyl-2-deoxy-α-D-galacto pyranoside (16.35 g, 27.45 mmol) in dry (molecular sieves) $CH_3OH$ (500 ml) was added a solution of sodium metal (6.7 g) in $CH_3OH$ (150 ml). This combined solution was stirred at room temperature for 18 hours then heated at reflux for 6 hours. The reaction solution was then stored at 0°. Solvent was removed by evaporation in vacuo to give a residue, which was partitioned between $CH_2Cl_2$ (500 ml) and $H_2O$ (250ml). The organic layer was separated, washed with $H_2O$ (3×250 ml), then dried over anhydrous $Na_2SO_4$. TLC at this point showed a small amount of residual mesyl derivative. Solvent was removed by evaporation in vacuo to give a pale yellow gum which was dried in vacuo. The product emitted a strong odor of methyl benzoate. A 500 g (75×275 mm)(1200 ml) column of silica gel was poured in $CH_2CL_2$ and the product was adhered to 50 g of silica gel. The column was eluted with $CH_2CL_2$ to remove front-running impurities. The product was eluted with $CH_3OH/CH_2Cl_2$ (1→3%). The column was then swept with 30% $CH_3OH/CH_2Cl_2$. Pooled fractions containing the various product components were evaporated in vacuo and the residues were dried in vacuo. Total major product fractions yield=10.02 g (74.3%).

Example 9

Benzyl 2-acetamido-3,6-di-O-benzyl-2,4-dideoxy-4-fluoro-α-D-glucopyranoside

To a stirred solution of DAST (N,N-diethylaminosulfur trifluoride) (25 g, 155 mmol) (Aldrich) in $CH_2Cl_2$ (75 ml), maintained at −20°±3° (dry ice-EtOH bath), was added, dropwise over one hour, a solution of benzyl2-acetamido-3,6-di-O-benzyl-2-deoxy-α-D-galactopyranoside (8.86 g, 18.023 mmol) in $CH_2Cl_2$ (200 ml). This solution was stirred at −20±3° for 40 minutes. Anhydrous pyridine (9 ml) was then added. The resulting solution was allowed to stir at room temperature for 3 hours, when internal temperature was again lowered to −20°. Absolute EtOH (35 ml) was now added dropwise, followed by $H_2O$ (40 ml). This mixture was allowed to stir at room temperature for 18 hours, then diluted with $CH_2Cl_2$ (300 ml) and $H_2O$ (300 ml). The organic layer was separated, washed with $H_2O$ (3×200 ml), then dried over anhydrous $Na_2SO_4$. Solvent was removed by evaporation in vacuo to give the crude product as an amber oil which was dried at room temperature in vacuo 18 hours. A 150 g silica gel column (42×280 mm) was poured in $CH_2Cl_2$ The crude product was adhered to 15 g of silica gel then added to the column, which was then eluted with $CH_2Cl_2$. A group of fast-running impurities which emerged initially was discarded. This was followed by product. All fractions were evaporated in vacuo to residues, which were dried in vacuo. Yield=6.44 g (72.4%).

Example 10

2-Acetamido-2,4-dideoxy-4-fluoro-D-glucopyranose

A solution of benzyl2-acetamido-3,6-di-O-benzyl-2,4-dideoxy-4-fluoro-α-D-glucopyranose (3.21 g, 6.51 mmol) in the HOAc (150 ml) containing 10% Pd/charcoal catalyst (4.3 g) was hydrogenated at 50–55 psig. Pressure dropped from 55 to 50 psig and was re-pressurized to 56 psig. Again, pressure dropped to approximately 50 psig. A small sample was withdrawn. The reaction appeared to have made a little progress, but much starting material remained as shown by TLC. Catalyst was removed by filtration through a layer of Celite, which was washed with $H_2O$ and EtOH. The filtrate was evaporated in vacuo to low bulk then again clarified by filtration through a layer of Celite. This filtrate was now evaporated in vacuo to a dry solid, which was dried in vacuo for 18 hours. Yield=2.57 g. The reaction was then re-started by dissolving 2.01 g (5.09 mmol) of the product in glacial HOAc (50 ml) containing 2.65 g of 10% Pd/charcoal catalyst, using a Parr shaker apparatus, to hydrogenate at 50 psig for 5 days. A sample was withdrawn, membrane-filtered, then evaporated in vacuo to a residue. This material was checked via TLC and the reaction appeared to have been successful, although a small amount of unknown material showed just ahead of the product. The remainder of the reaction catalyst was removed by filtration through a layer of Celite. The filtrate was evaporated in vacuo to a residue, which was dried in vacuo 18 hours; Yield=2.67 g. This material was now triturated in warm absolute EtOH (approx. 25 ml). Ether was added, in portions (250–300 ml). A tan solid appeared. The supernatent liquid was removed by decontation; the residue was dried in vacuo Yield=1.35 g (54.6%).

Example 11

2-acetamido-1,3,6-tri-O-acetyl-2,4-dideoxy-4-fluoro-D-glucopyranose

A solution of 2-acetamido-4-fluoro-2,4-dideoxy-D-glucopyranose (1.35 g, 6.048 mmol) in a mixture of pyridine (50 ml) and acetic anhydride (25 ml, 27 g, 264 mmol) was stirred at room temperature for 24 hours at which time no starting material but two close spots appeared by TLC. Stirring continued for another 15 hours. Solvent was then removed by evaporation in vacuo; the residue was now co-evaporated with toluene (4×50 ml) then dried in vacuo. This material was now adsorbed on 5 g of silica gel then placed on a silica gel column (45 g, 20×360 mm) poured in $CH_2Cl_2$/acetone (8:1). The column was eluted with 500 ml of $CH_2Cl_2$/acetone (8:1) followed by 500 ml of $CH_2Cl_2$/$CH_3OH$ (7:3). The product and trailing spots eluted immediately, with virtually no separation. The $CH_2Cl_2$/$CH_3OH$ flush produced a trailing spot. All were evaporated and dried in vacuo.

Since NMR data was ambiguous, and TLC indicated a mixture, the oil and foam fractions were combined and then re-chromatographed on a 25 g silica gel column poured in $CH_2Cl_2$. The column was eluted thus: (5 ml fractions).

TABLE 1

| Vol/Ml | $CH_2CL_2$ | acetone | $CH_3OH$ |
|---|---|---|---|
| 50 | 100% | — | — |
| 50 | 99 | 1% | — |
| 50 | 98 | 2 | — |
| 50 | 97 | 3 | — |
| 50 | 96 | 4 | — |
| 200+ | 95 | 5 | — |
| 200 | 50% | — | 50% |

Appropriate fractions containing the product were pooled, evaporated in vacuo and dried. Yield, 0.590 g (56.6% recovery, 27.9% yield).

Examples 12 to 15 demonstrate the pharmacological properties of preferred embodiments of the invention.

Example 12

Before conducting experiments with newly synthesized 3- and 4-F-GlcNAc the effects of 3- and 4-F-GlcNAc on the growth of a panel of human tumor cell lines as well as normal endothelial cells (i.e. $IC_{50}$ values) were first determined and compared with the original growth inhibitory action (9 Bernacki, R. J. et al. (1977) J. Supra. Stru., 7:235–250; 10 Sharma, M. and W. Korytnyk (1980) Carbohyd. Res., 79:39–51;11 Sharma, M. et al. (1990). Carbohyd. Res., 198:205–22). We found that the $IC_{50}$ values of the newly synthesized compounds were identical to those that were previously described for 3- and 4-F-GlcNAc synthesized by the original method.

Example 13

This example demonstrates the effects of 4-F-GlcNAc treatment on the expression and function of CLA/PSGL-1 as naturally expressed on human CLA+-T-lymphocytes. Using flow cytometry, we measured the level of CLA/PSGL-1 expression on 4-F-GlcNAc-treated CLA+ T-cells with the rat monoclonal Ab anti-human CLA HECA-452 and the mouse monoclonal Ab anti-human PSGL PL-1. Prior to expression analysis, we first examined the growth inhibitory effects of 4-F-GlcNAc on CLA+ T-cell cultures and determined that there was no inhibition of growth of cultures that were treated for 36 hr at concentrations less than 0.5 mM. Furthermore, to study the effects of 4-F-GlcNAc on the de novo synthesis of CLA, we initially treated CLA+ T-cells with *Vibrio cholerae* neuraminidase to cleave all terminal sialic acid residues, which are critical for recognition by HECA-452. Cells were treated with *Vibrio cholerae* neuraminidase (0.1 U/ml for 1 hr at 37° C.) and then re-cultured with 4-F-GlcNAc (0.05, 0.1 or 0.5 mM) for 30 hr prior to staining with rat 1 gM anti-CLA HECA-452 moAb or mouse IgG anti-PSGL-1 (PL-2). Only positive cells, which were those cells with fluorescence above background autofluorescence and fluorochrome-conjugated secondary Ab staining, were analyzed. This approach allowed for a direct assessment on the effects of 4-F-GlcNAc on CLA biosynthesis and circumvented the unknown turnover rate of CLA, which could lead to erroneous conclusions on 4-F-GlcNAc efficacy. We found that 4-F-GlcNAc treatment resulted in a marked, concentration-dependent decrease in HECA-452 epitopes on CLA+ T-cells, whereas recognition of PSGL-1 with peptide specific Ab PL-1 was minimally affected, with the except of the highest concentration (See Table 2). Since HECA-452 epitopes are located on PSGL-1, this data indicated that 0.05 and 0.1 mM 4-F-GlcNAc reduced the level of HECA-452 glycosylations on PSGL-1 without influencing protein synthesis or the quantity of PSGL-1 molecule.

TABLE 2

Flow Cytometric Analysis of HECA-452 Epitopes and PSGL-1 on 4-F-GlcNAc-Treated Human CLA+ T-Lymphocytes.

| Treatment Groups | HECA-452 Mean Channel Fluorescence | PSGL-1 Mean Channel Fluorescence |
|---|---|---|
| CLA+ T-cells untreated | 565 | 164 |
| CLA+ T-cells, neuraminidase (1 hr) | 27 | 118 |
| CLA+ T-cells, neuraminidase then recovery in PBS (36 hr) | 442 | 130 |
| CLA+ T-cells, neuraminidase then recovery in 0.05 mM 4-F-GlcNAc | 228 | 181 |
| CLA+ T-cells, neuraminidase then recovery in 0.1 mM 4-F-GlcNAc | 217 | 110 |
| CLA+ T-cells, neuraminidase then recovery in 0.5 mM 4-F-GlcNAc | 62 | 58 |

Example 14

Figure 3:
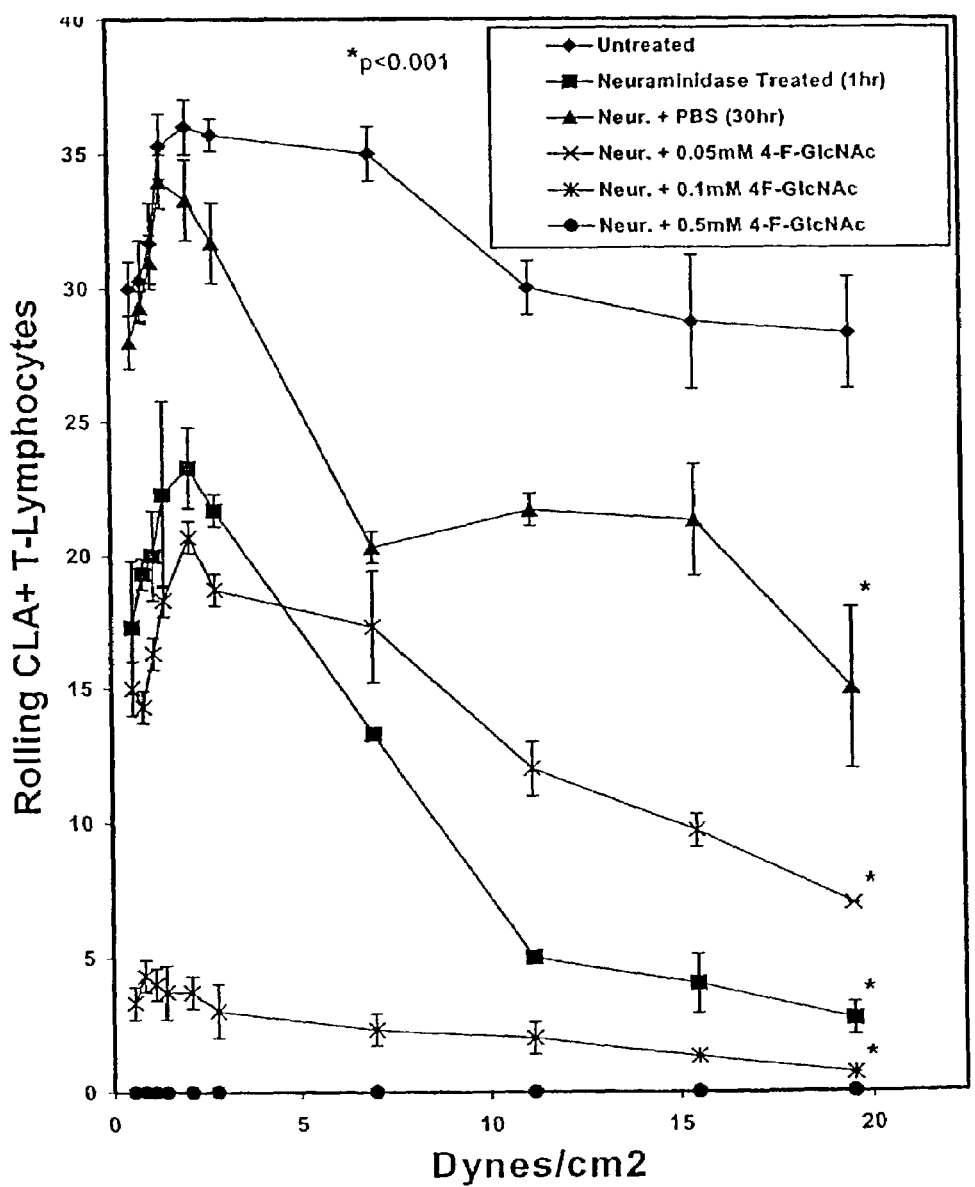
FIG. 3 illustrates the effect of 4-F-GlcNAc on P-selectin ligand activity of CLA+T-lymphocytes.
Figure 4:
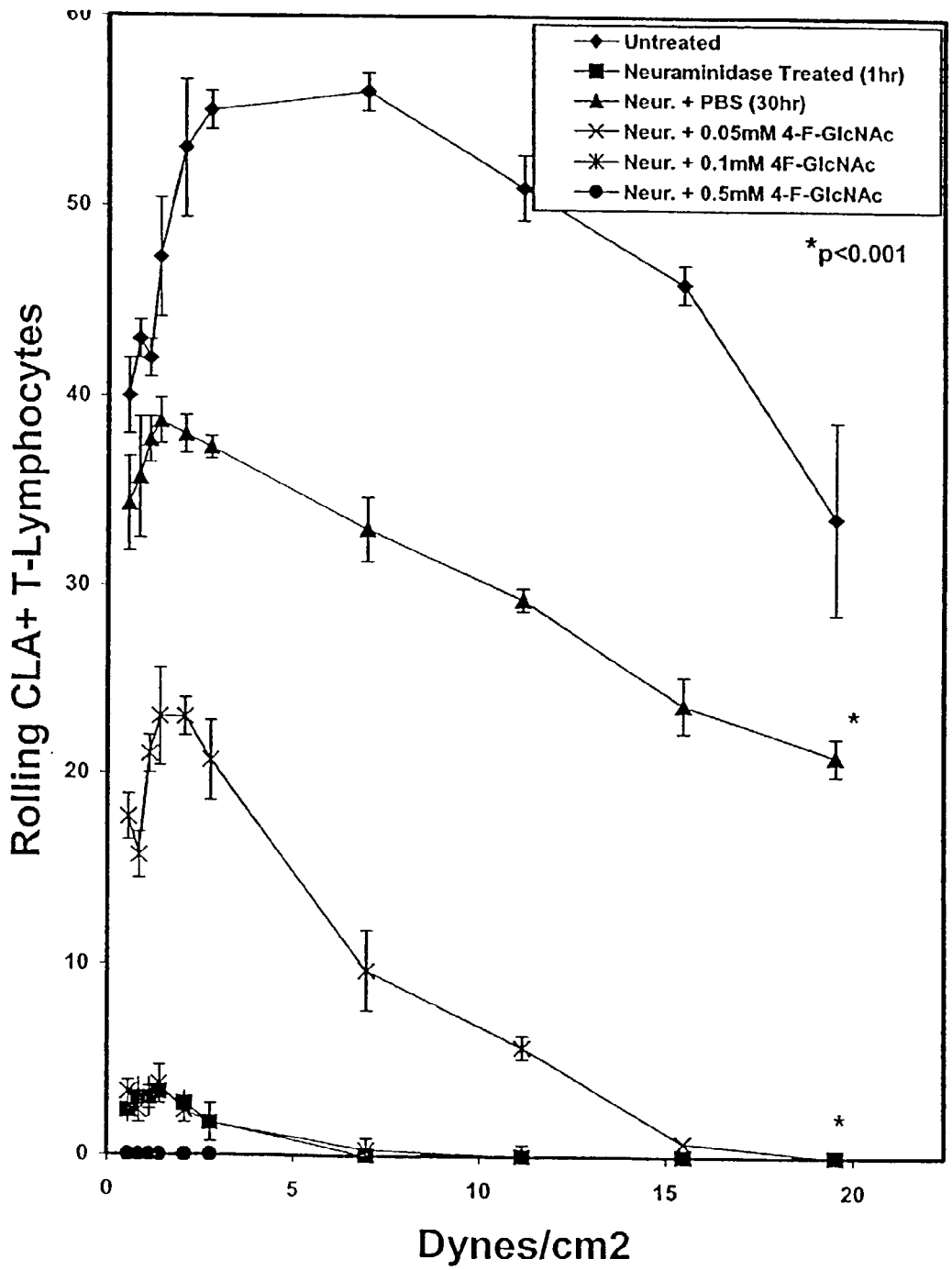
FIG. 4 illustrates the effect of 4-F-GlcNAc on E-selectin ligand activity of CLA+T-lymphocytes.

To analyze the affects of 4-F-GlcNAc on the function of CLA on human T-cells, we examined the ability of 4-F-GlcNAc-treated (0.05, 0.1, 0.5 mM for 30 hrs) CLA-+ T-cells cultures to engage with immobilized E- and P-selectin chimera in the parallel-plate flow chamber. As described for flow cytometric analyses (Example 13), cells were first pretreated with neuraminidase to remove terminal sialic acid residues required for HECA-452 reactivity and for E- and P-selectin ligand activity of CLA. This approach allowed for the assessment on de novo synthesized CLA molecules. We found a concentration-dependent reduction in CLA+ T-cell tethering and rolling on both P- and E-selectin chimera (See FIGS. 3 and 4). Neuraminidase treatment then 0.1 and 0.5 mM 4-F-GlcNAc treatment completely abolished CLA+ T-cell tethering and rolling mediated by P- or E-selectin (See FIGS. 3 and 4). Even at the lowest concentration of 0.05 mM 4-F-GlcNAc, the difference in cell rolling frequency of CLA+ T-cells was statistically significant when compared with the cell rolling frequency of cells that were allowed to recover from neuraminidase treatment in the presence of vehicle control PBS ($p<0.001$) (See FIGS. 3 and 4). Moreover, the shear resistance of cell rolling interactions was markedly reduced and the shear stress range was significantly narrowed. There was no cell rolling on E- or P-selectin chimeras that were pretreated with their respective functional blocking moAb or on E- or P-selectin chimeras in the presence of 0.5 mM EDTA, which both confirm the contribution of the selectin portion of the chimera supporting rolling adhesions. These data corroborate with flow cytometry analysis of CLA expression on 4-F-GlcNAc-treated CLA+ T-cells, providing firm evidence that 4-F-GlcNAc, at non-growth inhibitory concentrations, can modulate the expression, structure and function of CLA and inhibit tethering and rolling adhesive behavior.

In a similar set of experiments, we analyzed the effects of 4-F-GlcNAc on selectin ligand expression and function on the human hematopoietic cell line KG1a. KG1a cells express a distinct HECA-452-reactive CD44 glycoform that functions as both an E- and L-selectin ligand (Dimitroff, C. J. et al. (2001) J. Cell Biol., 53: 1277–1286; Dimitroff, C. J. et al. (2000) Proc. Nat. Acad. Sci., 97(25):13841–46; Sackstein, R. and Dimitroff, C. J. (2000) Blood, 96: 2765–74.), otherwise known as HCELL, respectively. This specialized glycoform represents a major E-selectin and the primary L-selectin ligand on normal CD34+ HPCs and on leukemic cells, and, therefore, is also implicated in the BM homing aspects and growth-related activities of HPCs in vivo, respectively (Id.). We first performed flow cytometric analysis of HECA-452 antigen and CD44 on 4-F-GlcNAc-treated KG1a cells. Using non-growth inhibitory concentrations, we treated KG1a cells, which were pretreated with 0.1 U/ml *Vibrio cholerae* neuraminidase, with 0.05, 0.1 or 0.5 mM 4-F-GlcNAc for 36 hr at 37° C. Cells were treated with *Vibrio cholerae* neuraminidase (0.1 U/ml for 1 hr at 37° C.) and then re-cultured with non-toxic concentrations of 4-F-GcNAc (0.05, 0.1 or 0.5 mM) for 30 hr prior to staining with rat 1 gM anti-CLA HECA-452 moAb or mouse IgG anti-PSGL-1 (PL-2). Only positive cells, which were those cells with fluorescence above background autofluorescence and fluorochrome-conjugated secondary Ab staining, were analyzed. We found that HECA-452 reactivity was sensitive to neuraminidase digestion and de novo re-expression of the HECA-452 epitopes was inhibited in a concentration-dependent manner (Table 3). However, there was no reduction in the expression of CD44, even at 0.5 mM 4-F-GlcNAc (Table 3), suggesting that glycosylation or synthesis of HECA-452 antigen on CD44, specifically, was interrupted. Though KG1a cellular glycosylation was most likely inhibited, the requirement for glycosylation in KG1a cel growth and protein synthesis was maintained at concentrations that modulated the structure of cell surface carbohydrates.

TABLE 3

Flow Cytometric Analysis of HECA-452 Epitopes and CD44 on Peracetylated 4-Fluorinated-Glucosamine (4-F-GlcNAc)-Treated Human Hematopoietic KG1a Cells.

| Treatment Groups | HECA-452 Mean Channel Fluorescence | CD44 % Positive Cell Staining |
|---|---|---|
| KG1a untreated | 152 | 99 |
| KG1a, neuraminidase (1 hr) | 43 | 100 |
| KG1a, neuraminidase then recovery in PBS (36 hr) | 146 | 100 |
| KG1a neuraminidase then recovery in 0.05 mM 4-F-GlcNAc | 112 | 100 |
| KG1a neuraminidase then recovery in 0.1 mM 4-F-GlcNAc | 108 | 100 |
| KG1a neuraminidase then recovery in 0.5 mM 4-F-GlcNAc | 43 | 100 |

Example 15

To study the effects of 4-F-GlcNAc on the function of the L-selectin binding activity of CD44 (HCELL), we employed the shear-based, Stamper-Woodruff adhesion assay to examine the ability of 4-F-GlcNAc-treated KG1a cells to support L-selectin-dependent lymphocyte adherence. This assay is utilized to specifically assess the shear-dependent binding interactions between L-selectin naturally expressed on lymphocytes and HCELL expressed on KG1a cells (Dimitroff, C. J. et al. (2000) Proc. Nat. Acad. Sci., 97(25):13841–46; Sackstein, R. and Dimitroff, C. J. (2000) Blood, 96: 2765–74.). Before treating KG1a cells with 0.05, 0.1 or 0.5 mM 4-F-GlcNAc, we first pretreated KG1a cells with *Vibrio cholerae* neuraminidase (0.1 U/ml for 1 hr at 37° C.) to cleave all terminal α2,3 sialic acid-bearing residues and eliminate all HCELL activity. Glutaraldehyde-fixed monolayers of KG1a cells that were first treated with *Vibrio cholerae* neuraminidase (0.1 U/ml for 1 hr at 37° C.) then re-cultured in the presence of 4-F-GlcNAc (0.05–0.5 mM) for 30 hr at 37° C. Metabolic inhibitors swainsonine, an inhibitor of α-mannosidase II, tunicamycin, an inhibitor of N-acetylglucosamine phosphototransferase, were also utilized to compare the relative potencies of known glycosylation inhibitors. Human peripheral blood lymphocytes ($5 \times 10^6$ cells/ml RPMI1640 w/o NaBicarbonate/5%FBS) were overlayed onto KG1a monolayers at 80 rpm for 30 min. at 4° C., and after gently washing in PBS, lymphocytes bound to cell monolayers were fixed in 3% glutaraldehyde. Re-expression of HCELL activity or HECA-452-reactive CD44 on KG1a cells was determined after 36 hr of 4-F-GlcNAc treatment. Bound lymphocytes were quantified at 100× magnification from a minimum of 5 fields from 2 slides, and the mean number of lymphocytes (standard error of the mean) was calculated.

TABLE 4

Effect of Peracetylated 4-Fluorinated Glucosamine (4-F-GlcNAc) on HCELL/CD44 Activity on Human Hematopoietic KG1a Cells in the Stamper-Woodruff Assay.

| Treatment Groups | Mean Lymphocyte Binding (SEM)$^2$ | % Inhibition |
| --- | --- | --- |
| KG1a neuraminidase (1 hr) | 4.2 (1.0) | 98* |
| KG1a, neuraminidase then recovery in PBS (36 hr) | 233.4 (8.8) | —* |
| KG1a neuraminidase then recovery in 0.05 mM 4-F-GlcNAc | 93.6 (7.1) | 60* |
| KG1a neuraminidase then recovery in 0.1 mM 4-F-GlcNAc | 50.6 (5.1) | 78* |
| KG1a neuraminidase then recovery in 0.5 mM 4-F-GlcNAc | 15.4 (3.0) | 94* |
| KG1a neuraminidase then recovery in 0.23 mM swainsonine | 60.7 (4.0) | 74* |
| KG1a neuraminidase then recovery in 0.02 mM tunicamycin | 3.0 (1.2) | 99 |

*$p < 0.001$; Student's paired t-test.

Compared with recovery in PBS, lymphocyte binding to KG1a cells treated with 4-F-GlcNAc was significantly abrogated ($p<0.001$) (Table 4). In comparison with a known metabolic inhibitor of complex type N-glycosylations, swainsonine, 4-F-GlcNAc was a more potent inhibitor of HCELL activity. However, tunicamycin, a highly potent inhibitor of the initial step of N-glycosylation and of cell growth, was a more potent inhibitor of HCELL activity than both swainsonine and 4-F-GlcNAc. L-selectin dependence was confirmed in all cases by either pretreating lymphocytes with functional blocking anti-human L-selectin moAbs LAM 1–3 (10 µg/ml), with PMA, which induces the shedding of L-selectin, (50 ng/ml) or performing the assay in the presence of 0.5 mM EDTA, all of which completely abrogated lymphocyte binding to KG1a cells.

Swainsonine is currently under clinical development as a chemotherapeutic agent against solid tumors (17,18), but its value as a carbohydrate inhibitor of leukocyte selectin ligand expression and control of both physiologic and pathologic leukocyte homing has not been appreciated. Because 4-F-GlcNAc is shown above to be a more potent selectin ligand inhibitor than swainsonine, the therapeutic potential of 4-F-GlcNAc, and likewise 3-F-GlcNAc, in the treatment of blood-borne cancers and leukocyte-associated dermatoses is heightened. Moreover, since 4-F-GlcNAc is a weak inhibitor of cell growth and glycosyltransferase levels and/or activities of target cells is much greater than baseline levels required for steady-state immunosurviellance of the skin (i.e. CTCL fucosyltransferase expression is markedly elevated compared with its expression in normal memory T-cells, communicated by Thomas S. Kupper, Harvard Medical School), it represents a highly selective compound with a broad therapeutic index and limited risk of side effects.

Example 16

General Methods

Unless otherwise described, the examples provided herein were performed using the following methods.

Antibodies. Enzymes, Metabolic Inhibitors and Radiochemicals.

Rat IgM anti-human CLA HECA-452 monoclonal antibody and FITC-rat IgM HECA-452 were purchased from BD PharMingen, Inc. (San Diego, Calif.). PerCP-mouse IgG$_1$, PerCP-mouse IgG anti-human CD4 (clone SK3) and PerCP-mouse IgG anti-human CD8 (SK1) were purchased from BD Biosciences, (San Jose, Calif.). Goat anti-mouse IgG, alkaline phosphatase (AP)-goat anti-rat IgM and AP-goat anti-mouse IgG were purchased from Southern Biotechnology Associates, Inc. (Birmingham, Ala.). Mouse IgG anti-human CD3 and mouse IgG anti-human PSGL-1 monoclonal antibody (PL-1 or PL-2) were purchased from Beckman Coulter, Inc. (Brea, Calif.). Mouse IgG anti-human PSGL-1 moAbs (clones 2G3, 4F9 and 4D8) were generously provided from Wyeth/Genetics Institute, Inc. (Cambridge, Mass.). *Vibrio cholerae* neuraminidase was purchased from Roche Molecular Biochemicals, Inc. (Indianapolis, Ind.). Human IgG, bromelain, tunicamycin, swainsonine, N-acetylglucosamine (GlcNAc) and benzyl-O-N-acetylgalactosamide (BAG) were from Sigma Chemical, Inc. (St. Louis, Mo.). Easy Tag™ [$^{35}$S]-protein labeling mix was purchased from NEN Life Science products, Inc. (Boston, Mass.). 2-Acetamido-1,3,6-tri-O-acetyl-4-deoxy-4-fluoro-D-glucopyranose (4-F-GlcNAc), which possesses a fluorine substitution at carbon-4 of the pyranose ring (FIG. 5A) and putatively blocks poly-N-acetyllactosamine elongation (31–34) (FIG. 5B and C), and tritiated 4-F-Glc[$^3$H]NAc (16 µCi/µmol) were synthesized and provided by the Chemical Resource Laboratory at Roswell Park Cancer Institute, Buffalo, N.Y.

Generation of Human Cutaneous Lymphocyte-Associated Antigen (CLA) Expressing T-cells Treated with Glycosylation Modifiers or Protease.

Human CLA$^+$ T-cells were prepared as previously described (3). Human peripheral blood mononuclear cells (PBMC) were isolated from citrated-whole blood by Histopaque-1077 (Sigma Diagnostics, Inc., St. Louis, Mo.) density-gradient centrifugation under pathogen-free conditions. PBMC were suspended in X-VIVO 15 serum free medium (BioWhittaker, Inc., Walkersville, Md.), plated on anti-human CD3-coated 24-well plates ($2 \times 10^6$ cells/well) and activated for 48 h at 37° C. Alternatively, as negative control for CLA expression, PBMC were suspended in RPMI 1640/10%FBS (Life Technologies, Grand Island, N.Y.) and activated on anti-CD3-coated plastic to produce T-cells expressing low levels of CLA (CLA$^{low}$ T-cells). For preparation of anti-human CD3-coated 24-well plates, goat anti-mouse IgG (5 µg/well in 500 µl 0.1 M NaCO$_3$, pH 9.6) was first added and incubated for 2 h at 37° C. After washing 3× with PBS, mouse anti-CD3 (0.1 µg/well in 500 µl PBS/2%FBS) was then added to each well, incubated for 2 h at 37° C., and plates were stored at 4° C. until ready for use. After cell activation on anti-CD3-coated plates, T-cells were harvested, suspended in X-VIVO 15 serum-free medium containing 5 ng/ml recombinant human IL-2, and re-plated in non-antibody-coated 24-well plates at $2 \times 10^6$ cells/well for 48 h at 37° C. This step was repeated 3 more times (48 hr intervals), and cells were examined for CLA, CD4 and CD8 expression by flow cytometry to confirm elevated CLA expression (99% CLA$^+$ vs. 18% on CLA$^{low}$ T-cells or on freshly isolated peripheral blood lymphocytes (PBL)) and frequency of CD4 (45% positive) and CD8 (62% positive) subsets before utilizing in functional adherence assays or in preparation of cell lysates.

For analysis of CLA expression on T-cells treated with glycoconjugate modifiers, CLA$^+$ T-cells were first pretreated with neuraminidase (0.1 U/ml at 37° C. for 1 h) to eliminate functional CLA and cleave all HECA-452 reactive epitopes from the cell surface (35–38). Since we wanted to investigate whether these compounds directly affected CLA expression and function, neuraminidase pretreatment followed by incubations with glycosylation modifiers allowed for examination of de novo synthesized CLA/HECA-452 epitopes re-expressed on the cell surface. After neuraminidase digestion, cells were then incubated with tunicamycin (0.02 mM) (an inhibitor of GlcNAc phosphotransferase, the initial step of N-glycosylation), swainsonine (0.23 mM) (an inhibitor of α-mannosidase II and complex-type N-glycosylation), 4-F-GlcNAc (0.05 mM) (putative inhibitor of poly-N-acetyllactosamine biosynthesis), BAG (an inhibitor of O-glycan biosynthesis) (<2 mM) or GlcNAc (5 mM) (negative control, naturally-occurring metabolic counterpart of 4-F-GlcNAc)for 30 h in the presence of human recombinant IL-2. Concentrations of tunicamycin and swainsonine were based on their N-glycan-inhibitory effects on human hematopoietic cell cultures, which possess identical growth rates as activated T-cells generated for these studies (35–38). Concentrations for BAG were selected based on maximal O-glycosylation inhibitory effects at non-growth inhibitory concentrations as previously reported (39). To determine a suitable concentration of 4-F-GlcNAc for examining glycoconjugate-modifying effects without influencing cell growth or protein synthesis, we performed preliminary growth inhibitory experiments of cells incubated with 4-F-GlcNAc for 2 cell doublings (~36 h) at 37° C. (cell viability assessed by Trypan-blue exclusion). It was found that 4-F-GlcNAc had an $IC_{10}$ value of >0.2 mM; thus, data generated from 4-F-GlcNAc treatments below 0.2 mM would not reflect inhibition of cell growth or protein synthesis (33, 34).

To assess the level of selectin ligand activity conferred by cell surface glycoprotein compared with the effects of glycosylation inhibitor treatments, cells were treated with bromelain (0.1% for 1 h at 37° C.), a protease known to remove membrane proteins including all P- and L-selectin ligand activity expressed on human hematopoietic cell membrane glycoproteins (i.e. PSGL-1 and HCELL) (35–38). Residual E-selectin ligand activity after bromelain treatment would, therefore, be indicative of activity contributed by a non-PSGL-1 glycolipid component (40–44). Bromelain-treated cells were then analyzed for both HECA-452 and PSGL-1 expression by flow cytometry. In addition, to further verify the complete disappearance of HECA-452 and PSGL-1 expression on the cell surface after bromelain treatment, membrane proteins were prepared as previously described by our laboratory (35–37) and analyzed for HECA-452 antigen and PSGL-1 polypeptide by Western blotting.

Flow Cytometric Analysis.

Flow cytometric analysis was performed on human leukocytes utilizing both direct and indirect immunofluorescence staining approaches. All cells utilized for these experiments were washed twice with cold PBS/2%FBS and suspended at $10^7$/ml PBS/1% FBS. Primary antibodies, anti-CLA (HECA-452), -CD4, -CD8, CD43 (L60) and PSGL-1 (PL-2) along with the appropriate isotype-matched control antibodies were incubated with the cells for 30 min on ice. Following two washes with PBS/2%FBS, cells were resuspended in PBS/1%FBS and fluorochrome-conjugated secondary antibodies (2 µl) and incubated for 30 min on ice. Cells were washed twice with PBS/2%FBS, resuspended in PBS and flow cytometry was performed on a FACScan apparatus equipped with an argon laser tuned at 488 nm (Becton Dickinson).

Cell Lysate Preparation and Immunoprecipitations.

For lysate preparation, cells (including radiolabeled cells) were washed 3× in ice cold PBS and lysed in buffer containing 150 mM NaCl, 50 mM Tris-HCl pH 7.4, 1 mM EDTA, 0.02% NaAzide, 20 µg/ml PMSF, Complete™ protease inhibitors cocktail tablets (Roche Molecular Biochemicals) and 2% NP-40 (250 µl/$10^8$ cells). Following 2 h incubation on ice, insoluble cellular debris was pelleted by centrifugation for 30 min at 10,000×g at 4° C. and solubilized protein lysate was collected and quantified by Bradford protein assay (Sigma Chemical). SDS was added to a final concentration of 1% in lysate preparations utilized for immunoprecipitation experiments.

For immunoprecipitation of PSGL-1, anti-PSGL-1 moAbs PL-2 2G3, 4F9 and 4D8 (2 µg each) were added to non-radiolabeled or radiolabeled cell lysates (containing 1% SDS) precleared in recombinant Protein G-agarose (Life Technologies) for 18 h at 4° C. on a rotator. Immunoprecipitations with mouse IgG isotype control at a similar Ab:lysate ratio were also performed to serve as negative controls. The antibody-lysate mixture was added to Protein G-agarose, pre-incubated with lysis buffer/2% NP-40/1% SDS/1% BSA, and incubated for >4 hr at 4° C. under constant rotation. Immunoprecipitates were washed 5× with lysis buffer/2% NP-40/1% SDS/1% BSA, 3× with lysis buffer/2% NP-40/1% SDS without BSA, and then boiled in reducing sample buffer for analysis.

SDS-PAGE/WesternBlotting, Lectin Blotting and Autoradiography.

For SDS-PAGE and Western blotting, cell lysates, membrane proteins or immunoprecipitates were diluted and boiled in reducing sample buffer, and separated on 7–9% SDS-PAGE gels. Resolved protein was transferred to Sequiblot™ PVDF membrane (Bio-Rad, Inc., Hercules, Calif.) and blocked with FBS for 1 hr at RT. Blots were incubated with rat IgM anti-human CLA HECA-452 (1 µg/ml), mouse IgG anti-human PSGL-1 moAbs PL-2 (1 µg/ml), 203, 4F9 and 4D8 (1 µg each/ml), or mouse IgG anti-human CD43 L60 (1 µg/ml) for 1 hr at RT. Isotype control immunoblots using either rat IgM or mouse IgG were performed in parallel to evaluate non-specific reactive proteins. After three washes with PBS/0.1%Tween-20 (10 min/wash), blots were incubated with the respective secondary Ab, AP-conjugated goat anti-rat IgM (1:400) or goat anti-mouse IgG (1:8000). AP substrate, Western Blue® (Promega, Madison, Wis.) was then added to develop blots.

For lectin blotting, cell lysates (25 µg/spot) were spotted onto methanol-permeabilized PVDF membrane and blocked in FBS for 1 h at RT. Blots were then probed with AP-*Canavalia ensiformis* agglutinin (ConA) (2.0 µg/ml PBS; specificity: α-mannose), AP-*Triticum vulgaris* (Wheat germ) agglutinin (WGA) (0.5 µg/ml PBS; specificity: terminal GlcNAc or GlcNAcβ1,4GlcNAc) or AP-*Lycopersicon esculentum* (tomato lectin) agglutinin (LEA) (1.0 µg/ml PBS; specificity: (Galβ1,4GlcNAc)n) for 1 h at RT (All lectins from EY Labs., Inc., San Mateo, Calif.). After washing 3× in PBS/0.1% Tween-20 and 1× in PBS (10 min each), blots were developed with Western Blue®.

For autoradiography, lysates were prepared from cells metabolically radiolabeled with Easy Tag™ [$^{35}$S]-protein labeling mix (100 µCi/ml) in complete X-VIVO 15 medium for 30 h or with 4-F-Glc[$^3$H]NAc (0.1 mM [16 µCi/µmol]) for 36 h in complete X-VIVO 15 growth medium. Radiolabeled lysates or immunoprecipitates were resolved on reducing SDS-PAGE gels and gels were dried and exposed to Kodak Biomax MR film (Rochester, N.Y.). Densitometric scans of both anti-PSGL-1 and isotype control immunoprecipitates resolved by SDS-PAGE were performed using NIH ImageJ software, and 8-bit grayscale values were plotted vs.

the length of the lane (from high molecular weight range to the dye front) using Microsoft® Excel.

TCA Precipitation of Radiolabeled Human CLA+ T-Cell Macromolecules.

Human CLA+ T-cells (5×10⁶ cells/ml complete X-VIVO 15 medium) were grown in the presence of 4-F-Glc[³H]NAc (0.025–1.0 mM; 16 µCi/µmol) for 12 to 36 h. Cells were then harvested, washed 2× in ice cold PBS and incubated with 10%TCA (250 µl/5×10⁶ cells) on ice for 30 min. Cellular precipitates were passed over Whatman GF/C microfibre glass paper (Fisher Scientific) under vacuum pressure and washed 5× with ice cold 5%TCA and 3× with ice cold ddH₂O. Filter paper was placed into scintillation fluid and counted by a Beckman LS6000IC Scintillation Counter (Beckman Coulter, Inc., Fullerton, Calif.). After determining the counting efficiency of a known amount of tritiated 4-F-Glc[³H]NAc, cpms were corrected to nmols (16 µCi/µmol 4-F-Glc[³H]NAc) and fluorosugar analog content expressed on per cell basis.

Parallel-Plate Flow Chamber Analysis.

Tethering and rolling of human T-cells on recombinant human E- and P-selectin-Ig chimera (provided by Dr. Robert Fuhlbrigge, Harvard Medical School) and human L-selectin-Ig (gift from Dr. Ray Camphausen, Wyeth/Genetics Institute, Inc., Cambridge, Mass.) were analyzed in the parallel-plate flow chamber under physiologic shear stress conditions (3). To prepare E- and P-selectin-Ig chimera spots, protein A (300 µg/15 µl 0.1M NaHCO₃) was adsorbed to Ten-twenty-nine™ Petri dishes for 2 h at 37° C. Human serum albumin (2 µg/ml PBS) then added and incubated for 2 h at 37° C. to block non-specific binding sites. E-selectin-Ig (50 ng/50 µl PBS) or P-selectin-Ig (50 ng/50 µl PBS) solutions was pipetted directly over the pre-existing protein A spots for 18 h at 4° C. To prepare L-selectin-Ig spots, L-selectin-Ig (300 ng/15 µl PBS) or isotype control human IgG (300 ng/15 µl) were adsorbed directly to plastic (non-protein A-coated) for 18 h at 4° C. and blocked in 100% FBS for 2 h at 4° C.

CLA+ T-cells or freshly isolated PBL were treated with neuraminidase and metabolic glycosylation inhibitors or with protease (bromelain) as described above, washed twice in HBSS, suspended at 2×10⁶/ml in HBSS/10 mM HEPES/2 mM CaCl₂ (H/H/Ca++) and infused into the chamber over selectin chimeras. Protease treatment was performed to control for residual E-selectin activity not attributable to the expression of CLA on a protein scaffold. Cell tethering was permitted at 0.6 dynes/cm² for 1 min, then stepwise increments in shear stress every 15 sec were employed to a final shear stress level of 60 dynes/cm². The number of cells rolling/viewing field (at 100× magnification) was quantified at each level of shear stress in triplicates for a minimum of three experiments. All experiments were observed in real time and videotaped for offline analysis. Negative control experiments were performed in parallel, wherein cell binding was examined in H/H adhesion assay medium containing 5 mM EDTA as well as assaying cell binding to human IgG isotype control.

Example: 17

4-F-GlcNAc and BAG Prevents the Expression of HECA-452 Epitopes on PSGL-1

To examine the effects of glycosylation inhibitors on de novo synthesis of HECA-452 expression, T-cell cultures were treated with *Vibrio cholerae* neuraminidase to cleave terminal sialic acid residues critical for HECA-452 recognition and cellular selectin ligand activities (37, 38). This approach allowed for direct assessment on the effects of the glycosylation inhibitor on CLA biosynthesis and obviates the contribution of pre-formed CLA on the cell surface. Cells were then re-cultured in the presence of glycosylation inhibitor, diluent control (PBS) or molecular control (GlcNAc) for 30 hr and then harvested for CLA expression and functional analysis. By Western blot analysis, it was found that tunicamycin, BAG and 4-F-GlcNAc treatments following neuraminidase digestion resulted in a marked reduction in de novo synthesized HECA-452 epitopes on PSGL-1, which resolves as a dimer (220 kDa) and monomer (140 kDa) form (FIG. 6A) (3, 36, 37). Recovery of HECA-452 expression on cells grown in PBS, swainsonine or GlcNAc (drug control) was not affected. Data from preliminary experiments showed that BAG treatments at concentrations below 1.0 mM and tunicamycin treatment below 0.015 mM had minimal effects on HECA-452 expression (data not shown). On a molar basis, though tunicamycin was 2.5-fold more potent than 4-F-GlcNAc at lowering HECA-452 expression, 4-F-GlcNAc was more potent than BAG. Notably, whereas PSGL-1 expression in tunicamycin-treated cells was ablated, 4-F-GlcNAc had no effect on PSGL-1 expression itself (FIG. 6B), showing the ability of 4-F-GlcNAc to selectively inhibit glycosylation without interfering with homeostatic pathways of protein synthesis and cell growth. To assess the duration of anti-carbohydrate effects on HECA-452 expression on PSGL-1, cells treated with 4-F-GlcNAc for 30 h and were then re-cultured in non-4-F-GlcNAc-containing medium for 72 h. By HECA-452 immunoblotting, it was found that HECA-452 expression on PSGL-1 was suppressed for the first 48 h with re-expression thereafter, suggesting that the lipophilicity of 4-F-GlcNAc results in maximal uptake during exposure to cells, and, once converted to a nucleotide sugar (which is not exported from a cell), results in metabolic inhibition of selectin ligand synthesis for <48 h.

To further analyze O-glycan inhibitory effects and help assess the specificity of decreases in HECA-452 epitopes displayed by core 2 O-glycans on PSGL-1, we blotted lysate from BAG-treated cells with moAb L60, which recognizes a sialylated epitope expressed on O-glycans of CD43. BAG treatment resulted in complete abrogation of L60 reactivity (FIG. 6C). Interestingly, tunicamycin also reduced L60 recognition (FIG. 6C), suggesting a general inhibitory effect on cellular protein synthesis. Furthermore, 4-F-GlcNAc did not affect L60 reactivity, indicating that 4-F-GlcNAc did not affect O-glycosylation per se. Because 4-F-GlcNAc resulted in decrements in HECA-452 epitopes that reside on poly-N-acetyllactosamine backbones displayed by core 2 O-glycosylations on PSGL-1 (FIG. 2A), unchanged L-60 reactivity of CD43 from lysates of 4-F-GlcNAc-treated cells suggests that L-60 epitopes do not reside on poly-N-acetyl-lactosamine backbone(s) (45, 46).

Figure 7:
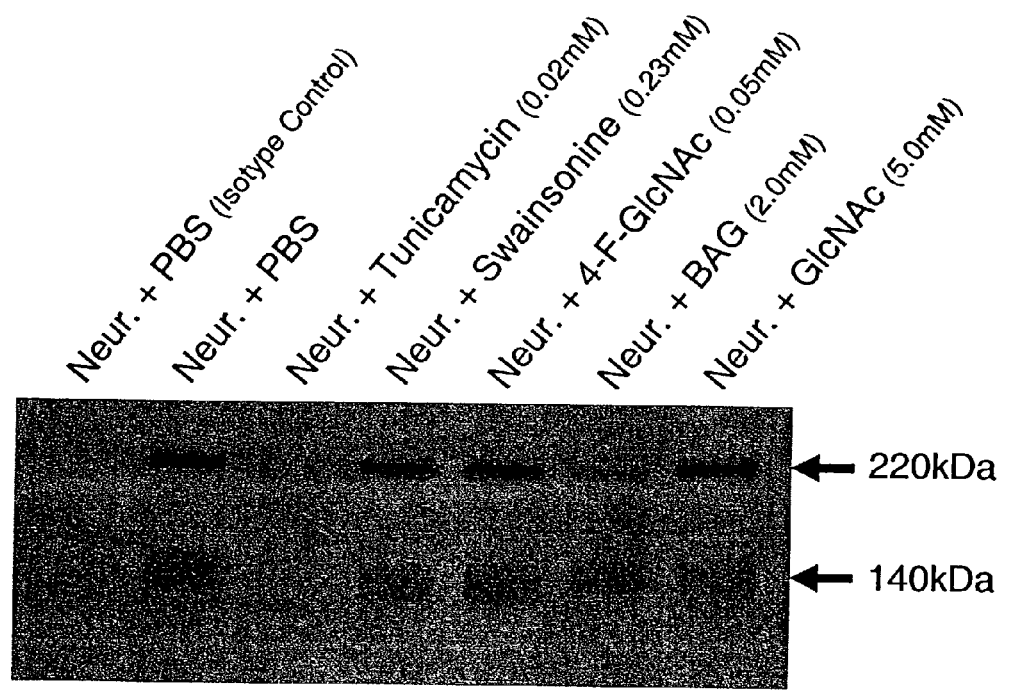
FIG. 7 is a photograph of an autoradiograph showing PSGL-1 isolated from metabolically radiolabeled CLA T-cells treated with glycosylation inhibitors.

To address the possibility of tunicamycin affecting the blotting capacity of PSGL-1 with anti-PSGL-1 moAbs, which could account for the lack of detection of PSGL-1 polypeptide by Western blotting (FIG. 6B), autoradiography of PSGL-1 immunoprecipitated was performed from cells metabolically radiolabeled with [³⁵S]-protein labeling mix concurrent with glycosylation inhibitor treatment. PSGL-1 expression on cells grown in tunicamycin was completely eliminated, indicating that ablation of HECA-452 epitopes was due to inhibition of PSGL-1 biosynthesis (FIG. 7). There was also a slight reduction in the incorporation of ³⁵S-protein labeling mix into PSGL-1 from cells treated with BAG, while the level of radioactive PSGL-1 isolated from cells grown in swainsonine or 4-F-GlcNAc was not changed compared with PSGL-1 from cells grown with PBS (diluent control) or GlcNAc (drug control) (FIG. 7).

Example 18

Suppression of Selectin Ligand Activities on Human CLA+ T-Cells

Figure 8:
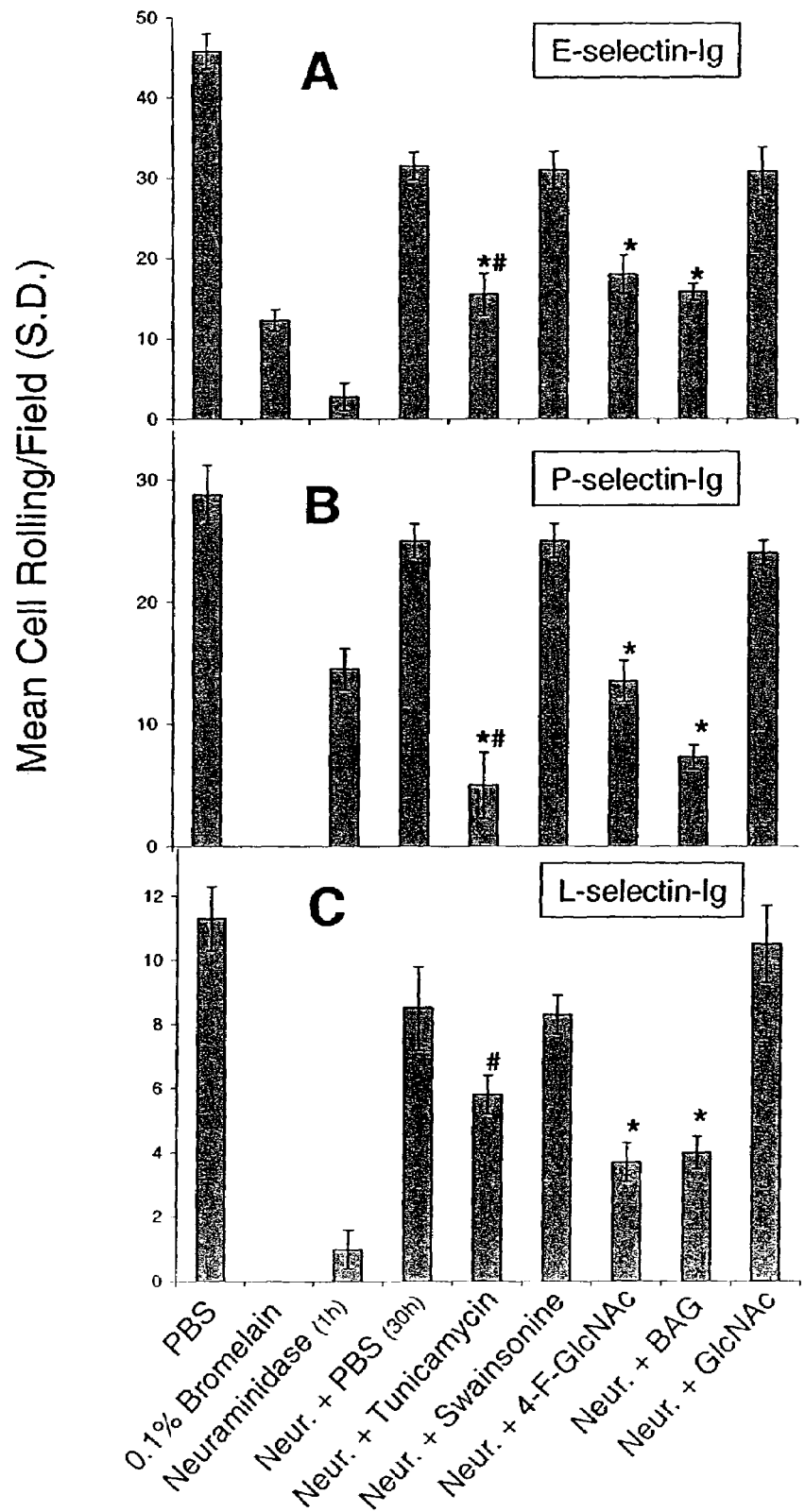
FIG. 8A is a bar chart showing the effects of glycosylation inhibitors on human CLA T-cell Rolling on E-selectin.
FIG. 8B is a bar chart showing the effects of glycosylation inhibitors on human CLA T-cell Rolling on P-selectin.
FIG. 8C is a bar chart showing the effects of glycosylation inhibitors on human CLA T-cell Rolling on L-selectin.

Utilizing the parallel-plate flow chamber under physiologic shear stress conditions, E-, P- and L-selectin ligand activities of human CLA+ T-cells treated were analyzed in an identical manner as cells prepared for Western blotting and autoradiography studies. Human CLA+ T-cells grown in PBS or GlcNAc (drug control) for 30 h following neuraminidase digestion resulted in a >80% recovery of selectin ligand activities, which were all inhibitable by adding 5 mM EDTA to the adhesion assays medium (FIG. 8). E-selectin and L-selectin ligand activities of negative control CLA$^{low}$ T-cells grown in RPMI-1640/10% FBS or freshly isolated PBL were considerably less than CLA+ T-cell activities (25% of CLA+ T-cell activity), while P-selectin ligand activities were not different from CLA+ T-cells (data not shown). At 2.0 dynes/cm$^2$, we observed significant reductions in rolling adhesions on E-, P- and L-selectin chimeras of cells treated with tunicamycin, 4-F-GlcNAc and BAG (p<0.01; Student's t-Test). However, inhibition of PSGL-1 expression in tunicamycin-treated cells (as shown in FIGS. 6B and 7) may explain for the marked decrement in selectin binding. Swainsonine had no effect on cell rolling on selectins, suggesting that complex-type N-glycans, particularly on PSGL-1, do not contribute to selectin ligand activities. Together, these observations indicate that functional modulation of selectin ligand activities with 4-F-GlcNAc and BAG directly correlate with inhibitory effects on HECA-452 expression on PSGL-1 and that selectin-binding determinants are displayed by core 2 O-glycans.

Importantly, treatment of cells with the protease, bromelain, completely eliminated PSGL-1 expression, as determined by flow cytometry (FIG. 9 Panels A and B), as well as P- and L-selectin ligand activities (FIG. 8), confirming that PSGL-1 is the primary glycoprotein P-/L-selectin ligand on CLA+ T-cells. However, though PSGL-1 was completely removed by bromelain digestion (FIG. 9 Panels A and B), E-selectin ligand activity (<25% of control) was observed (FIG. 8). This remaining E-selectin ligand activity of CLA+ T-cells parallels that of the baseline E-selectin ligand activity of CLA$^{low}$ T-cell or of fresh PBL (<25% of CLA+ T-cell activity), and likely reflects glycolipid E-selectin ligand activity. Notably, flow cytometry analysis of PSGL-1 and HECA-452 expression on CLA$^{low}$ T-cells or PBL after bromelain digestion indicated that HECA-452 expression was relatively unchanged, whereas PSGL-1 levels were completely abolished (FIG. 9 Panel A), indicating that HECA-452 expression on glycolipids is robust, though these structures contribute only a minor component of functional E-selectin binding that does not correlate with lymphocyte skin-homing and CLA/PSGL-1 expression. Though it was expected that tunicamycin and BAG would not lower E-selectin ligand activity below that of protease treatment alone (as these inhibitors are glycoprotein specific), the finding that 4-F-GlcNAc did not reduce E-selectin ligand activity below that of protease-treatment, as well, may reflect a selectivity for incorporation of 4-F-GlcNAc into poly-N-acetyllactosamines displayed by proteins. Presence of protease-resistant HECA-452 epitopes and E-selectin ligand activity, distinct from reductions due to 4-F-GlcNAc decrement, suggest that N-acetyllactosamine structures on glycolipids, such as neolacto glycosphingolipids, may not be affected by 4-F-GlcNAc treatment.

Example 19

Figure 10:
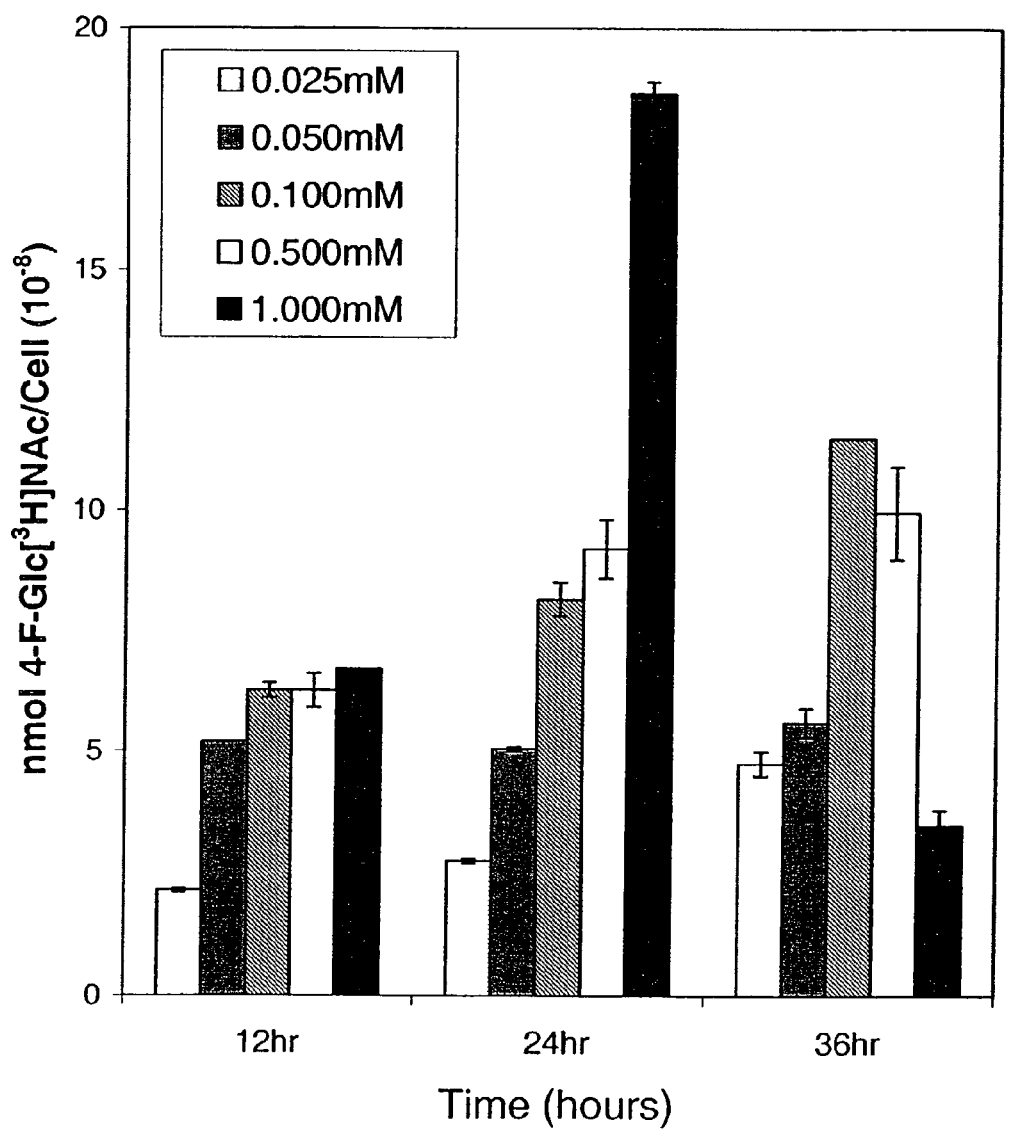
FIG. 10 is a bar chart showing incorporation of 4-F-Glc [³H]NAc into TCA-precipitated macromolecules isolated from human CLA+ T-cells.

4-F-GlcNAc Functions as a Metabolic Modulator of Poly-N-acetyllactosamine Synthesis and Selectin-Binding Determinants by Direct Incorporation into CLA Prior studies evaluating the inhibitory efficacy of 4-F-GlcNAc on human tumor cell binding to lectins indicate that 4-F-GlcNAc inhibits poly-N-acetyllactosamine synthesis and resultant terminal N-acetylneuraminic acid or galactose-bearing structures (33, 34). Even though protein synthesis and cell growth are unaffected by 4-F-GlcNAc at concentrations that are glycosylation-inhibitory, there is little direct evidence on the mechanism of anti-carbohydrate action. To help determine whether 4-F-GlcNAc is directly incorporated into glycoconjugates and reason for the observed reductions in terminal glycan decorations or HECA-452 expression on human CLA+ T-cells, we performed metabolic radiolabeling of CLA+ T-cells with tritiated 4-F-GlcNAc (4-F-Glc[$^3$H]NAc) and quantified the amount of 4-F-Glc[$^3$H]NAc incorporated into TCA-precipitated macromolecules on a per cell basis. In a concentration-dependent manner, it was found that 4-F-Glc [$^3$H]NAc was incorporated into TCA-precipitated macromolecules (FIG. 10). In addition, inhibition of cell growth and metabolic activity after 36 h incubation with 1.0 mM 4-F-Glc[$^3$H]NAc was noted, resulting in a significant reduction in cell frequency (<25% cell number at time 0) and a lower level of radioactivity in TCA-precipitated macromolecules (FIG. 10).

To demonstrate that modulation of CLA by 4-F-GlcNAc treatment was specifically due to the direct incorporation into PSGL-1, radiodetection of PSGL-1 immunoprecipitated from 4-F-Glc[$^3$H]NAc-labeled CLA+ T-cell lysates was performed. Though the low specific activity of 4-F-Glc[$^3$H]NAc prevented a strong signal after a 28-day exposure time, autoradiography and scanning densitometry revealed that both dimer (220 kDa) and monomer (140 kDa) forms of PSGL-1 were still detectable, while isotype control immunoprecipitates did not contain any radiolabeled PSGL-1 (FIG. 11 Panels A and B, Lane 2). These data indicate that termination of poly-N-acetyllactosamine extension and sialo-fucosylations (i.e. HECA-452 epitopes) on PSGL-1 by 4-F-GlcNAc treatment is due to inhibition of UDP-galactose (donor) linkage to the carbon 4-position of 4-F-GlcNAcβ1–3 Gal-R (acceptor).

To analyze and identify the glycan modifications on CLA+ T-cells treated with 4-F-GlcNAc, lectin blotting experiments were performed with ConA (Specificity: α-mannose), WGA (Specificity: terminal GlcNAc or GlcNAcβ1,4GlcNAc) and LEA (Specificity: {Galβ1,4GlcNAc}$_n$). These experiments confirmed the expected inhibitory effects on glycosylation by swainsonine and tunicamycin. In comparison with cells grown in PBS or GlcNAc (negative controls), it was found that ConA, WGA and LEA staining of lysates prepared from tunicamycin-treated cells were eliminated (FIG. 12). ConA staining of lysates from swainsonine-treated cells was enhanced, while there was no effect on ConA staining by 4-F-GlcNAc or BAG treatment (FIG. 12) compared with PBS or GlcNAc treatments. Furthermore, LEA staining of lysates from 4-F-GlcNAc-treated cells was notably diminished, whereas WGA staining was elevated (FIG. 12) compared with PBS, swainsonine, BAG or GlcNAc treatments. Interestingly, BAG treatment did not affect LEA staining, suggesting that residual poly-N-acetyllactosamine units on N-glycans are sufficient for observable LEA staining and that 4-F-GlcNAc was inhibiting poly-N-acetyllactosamines on O-glycans and N-glycans. These data confirmed the expected changes in glycosylation due to swainsonine treatment wherein α-mannosidase is inhibited and thus ConA staining (i.e. level of α-mannose residues) was increased. More importantly, reduction in poly-N-acetyllactosamine structures (LEA staining) due to 4-F-GlcNAc treatment corroborated with previous findings on 4-F-GlcNAc glycan modulation (34), and an elevation in WGA staining in conjunction with 4-F-Glc[$^3$H]NAc incorporation data into CLA strongly suggest that 4-F-GlcNAc acts as a terminator of poly-N-acetyllactosamine elongation. Though the presence of fluorine at the carbon-4 position of 4-GlcNAc may block glycosidic linkage to UDP-Gal, recognition of terminal 4-F-GlcNAc residues by WGA was not affected.

Example 20

4-F-GlcNAc inhibition of E- and P-Selectin-Binding of Murine TH1 Cells In-vitro

Figure 13:
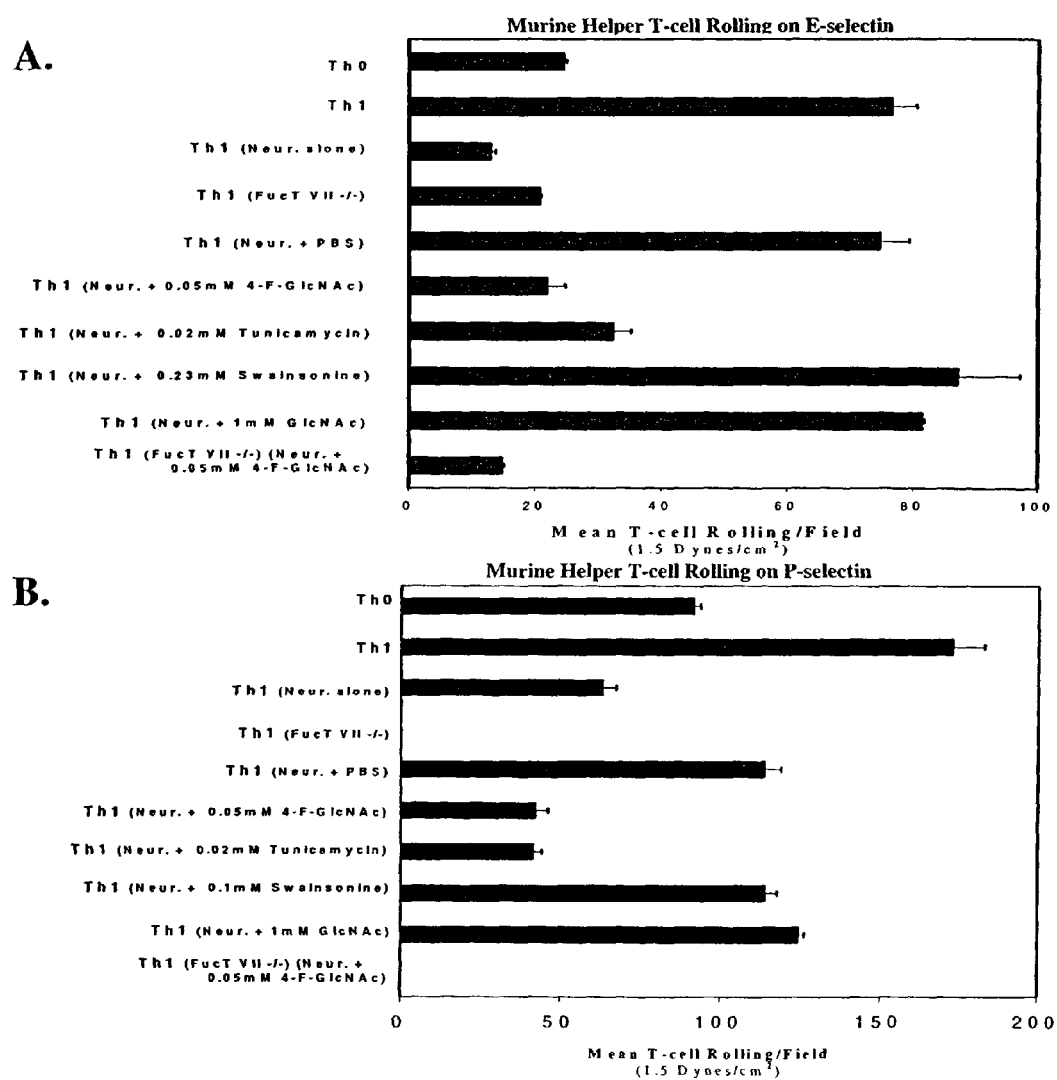
FIG. 13A is a bar chart showing the results of flow chamber anaylsis of E-selectin binding on murine Th1 cells.
FIG. 13B is a bar chart showing the results of flow chamber anaylsis of P-selectin binding on murine Th1 cells.

The example demonstrates the effects of 4-F-GlcNAc treatment on E- and P-selectin-binding properties of in vitro-derived murine Th1 cells. CD4+ splenocytes were isolated from C57BL-6 mice by anti-murine CD4 L3T4 magnetic bead technology (Miltenyi Biotec) according to manufacturer's protocol. CD4+ splenocytes (99% purity as determined by flow cytometry) were plated at $2 \times 10^6$ cells/ml/well on anti-murine CD3 and anti-murine CD28 (1 µg each/well in 24-well plates) for 48 h in the presence or absence of murine IL-12 (10 ng/ml) and anti-murine IL-4 moAb 11B11 (10 µg/ml). Culturing murine T helper cells in the presence of murine IL-12 and anti-murine IL-4 produces selectin binding Th1 cells by up-regulating FucTVII (69, 70) and core 2 enzyme (43–45, 71, 72), both critical for selectin ligand synthesis (i.e. decoration of PSGL-1 (67, 68)), and prevents the production of non-selectin binding Th2 cells (67–72). Th1 cells were also generated from mice deficient in α1,3 fucosyltransferase, FucTVII, and served as negative controls (33, 38, 40). Cells were harvested and re-plated at $2 \times 10^6$cells/ml on non-Ab coated plastic with murine IL-2 (20 ng/ml) in the presence or absence of murine IL-12 (10 ng/ml) and anti-murine IL-4 moAb 11B11 (10 µg/ml) for 48 h. After repeating this step 2 more times, cells, which possess a similar growth rate as human CLA+ T-cell cultures (~18 h doubling time), were harvested after day 8 for functional selectin binding analysis. Glycosylation inhibitors were added to cultures on day 6.5 for 30 hr, after first treating cells with neuraminidase (0.1 U/ml for 1 hr at 37° C.) to remove all cell surface terminal sialic acid resides and E and P-selectin ligand activity. Since selectin ligands are dependent on terminal sialic acid (α2,3 N-acetylneuraminic acid) for activity, this approach allowed for analysis of de novo synthesized selectin ligands in the presence of 0.05 mM 4-F-GlcNAc, N-glycan inhibitors, 0.23 mM swainsonine and 0.02 mM tunicamycin, and 1 mM GlcNAc (negative control). Neuraminidase treatment alone decreased E and P-selectin ligand activity to baseline levels expressed by non-Th1 cells (Th0) or FucTVII −/− Th1 cells (See FIG. 13A and B). Recovery of E- and P-selectin ligand activities of Th1 cells cultures in 4-F-GlcNAc or tunicamycin was completely inhibited, while recovery in PBS, GlcNAc or swainsonine had no effect (See FIG. 13A and B). Flow cytometric analysis of PSGL-1 and an O-glycan-dependent epitope on activated CD43, which directly correlates with core 2 O-glycan synthesis and selectin binding function of PSGL-1 (45, 71, 72), revealed that tunicamycin lowered the expression of both PSGL-1 and O-glycan epitope on CD43, suggesting that tunicamycin affected the re-expression of PSGL-1 (i.e. selectin ligand scaffold) and CD43 polypeptide. 4-F-GlcNAc treatment, on the other hand, did not significantly reduce PSGL-1 expression, yet markedly reduced the expression of O-glycan glycosylation on activated CD43 as determined FACS analysis of moAb antimurine O-glycosylated CD43 clone1B11 (data not shown). Collectively, these demonstrate the requirement for core 2 O-glycosylation and FucTVII and PSGL-1 expression for Th1 cell binding to E- and P-selectin and further demonstrate that 4-F-GlcNAc inhibits core 2 O-glycosylation (i.e. elongation of poly-N-acetyllactosamine chain) and subsequent synthesis of terminal sialyl Lewis X structures critical for E- and P-selectin binding. Additionally, 4-F-GlcNAc inhibitory activity on Th1 cell glycosylation was noted at a non-growth and non-protein inhibitory concentration.

Example 21

4-F-GlcNAc Inhibition of Inflammation In-Vivo

This example demonstrates the anti-inflammatory effects of 4-F-GlcNAc in vivo. Previous studies evaluating the anti-tumor and anti-metastatic effects of fluorinated hexosamine analogs and 3 or 4-F-GlcNAc, specifically, indicate that the dose limiting toxicity was ~250 mg/kg×6 days and that i.p. administration of these sugar analogs was an efficacious mode of delivery. Thus, in these studies, a maximal dose of 250 mg/kg as well as 100 and 50 kg/mg doses were used in order to make both toxic and efficacy assessments of fluorinated hexosamine analog anti-inflammatory effects. To induce delayed type hypersensitivity (DTH), C57BL6 mice were sensitized on their abdomen on days 0 and 1 with 25 µl of 0.5% 2,4-dinitrofluorobenzene (DNFB) (i.e. hapten) in a 4:1 solution of acetone to olive oil (vehicle). Negative control mice were sensitized with vehicle alone. Mice were then treated from days 0–6 with drug vehicle (0.9% saline), 50 mg/kg 4-F-GlcNAc, 100 mg/kg 4-F-GlcNAc, 250 mg/kg 4-F-GlcNAc or 250 mg/kg GlcNAc (negative sugar control). Hapten-induced inflammation was then promoted on day 6 by challenging the mice with 10 µl of 0.25% DNFB on both sides of the right ear and mice also received 10 µl of vehicle alone on both sides of the left ear as a negative inflammatory control. Ear swelling responses were measured 24 h later on day 7 and subtracted from baseline measurements that were recorded on day 6. In mice that received sensitizing and challenging hapten, both 100 and 250 mg/kg doses of 4-F-GlcNAc completely abrogated the inflammatory response, though, as expected, some toxicity was observed in mice dosed at 250 mg/kg as evidenced by the reduction in body weight (~5%) and total white cell counts (60% of drug controls) (See FIG. 10, Panel A). A 5-fold lower dose (50 mg/kg 4-F-GlcNAc) also caused a statistically significant diminution in the inflammatory response (p<0.0002, Student's paired t-Test) and did not affect mouse body weight or WBC counts, while negative drug control (GlcNAc) treatment had no anti-inflammatory effect, and, as expected, inflammatory responses in FucTVII −/− mice were minor and were further reduced with 4F-GlcNAc treatment (See FIG. 10, Panel A).

Histological analysis of right ears from mice receiving sensitizing and challenging hapten doses that were treated with saline vehicle control did show the presence of lymphocytic infiltrate and amount of lymphocytic infiltrate corresponded to ear swelling measurements (See FIG. 14 Panel B). These data indicated that: 1.) 250 mg/kg/d×6 4-F-GlcNAc was therapy-limiting, 2.). i.p. administration of 4-F-GlcNAc was an effective mode of delivery, and 3.) 100 and 50 mg/kg/d×6 days 4-F-GlcNAc were well-tolerated and suppressed an antigen-dependent inflammatory response by preventing the trafficking of Th1 cells to inflamed skin, a process mediated by selectin-binding glycosylations on PSGL-1 and by E- and P-selectin on dermal vascular endothelium.

Example 22

Effect of 4-F-GlcNAc on Migration of Langerhans Cells to Draining Lymph Nodes

Six to eight-week old C57BL/6 mice from Charles River Laboratories (Wilmington, Mass.) were housed in pathogen-free conditions in the animal facility at the Harvard Institutes of Medicine and utilized in these experiments. For analysis of LC migration to draining lymph nodes and antigenic presentation by dendritic cells (DC), right ears of mice were painted with 25 µl of 0.5% FITC, a contact sensitizing agent dissolved in acetone-dibutyl phthalate vehicle (1:1 v/v), while left ears were painted with 25 µl of vehicle alone. After 30 h, regional auricular/cervical lymph nodes draining right or left ears, respectively, were isolated and single cell suspensions were prepared. To enrich for DC, cell suspensions were subjected to Optiprep™ (Accurate Chemicals, Westbury, N.Y.) discontinuous gradient centrifugation. Cell preparations of ipsilateral lymph nodes from 4 mice were combined and incubated with PE-labeled hamster IgG1, γ anti-mouse CD11c, the integrin $α_x$-chain and murine dendritic cell marker (clone HL3; PharMingen, Inc., San Diego, Calif.) for 30 min. on, ice and washed 3-times with PBS/2% FBS and suspended in PBS for flow cytometric analysis using a FACScan (Becton Dickinson, San Jose, Calif.). Cell staining with isotype control PE-hamster IgG1, λ; (PharMingen, Inc.) was also performed to control for PE-anti-CD11c binding specificity. Furthermore, for double staining analysis of PE-anti-CD11c DC presenting FITC, FITC and PE intensity compensation settings were adjusted to PE-labeled rat IgG 2b, κ anti-mouse CD4 (clone L3T4; PharMingen, Inc.) or FITC-labeled rat IgG1, κ anti-mouse-CD8b.2 (Ly-3.2) (clone 53-5.8; PharMingen, Inc.) positive cell staining. Positive cells stained with PE-anti-CD11c were gated and analyzed for FITC expression.

To study the effects of 4-F-GlcNAc on LC migration to draining lymph nodes and DC presentation of FITC, mice were treated i.p. daily with 50, 100, or 250 mg/kg 4-F-GlcNAc (in 0.9% saline) for 3 days prior to sensitization with 0.5% FITC. There were duplicate groups/dose and 4 mice/group from a minimum of two experiments.

Figure 15:
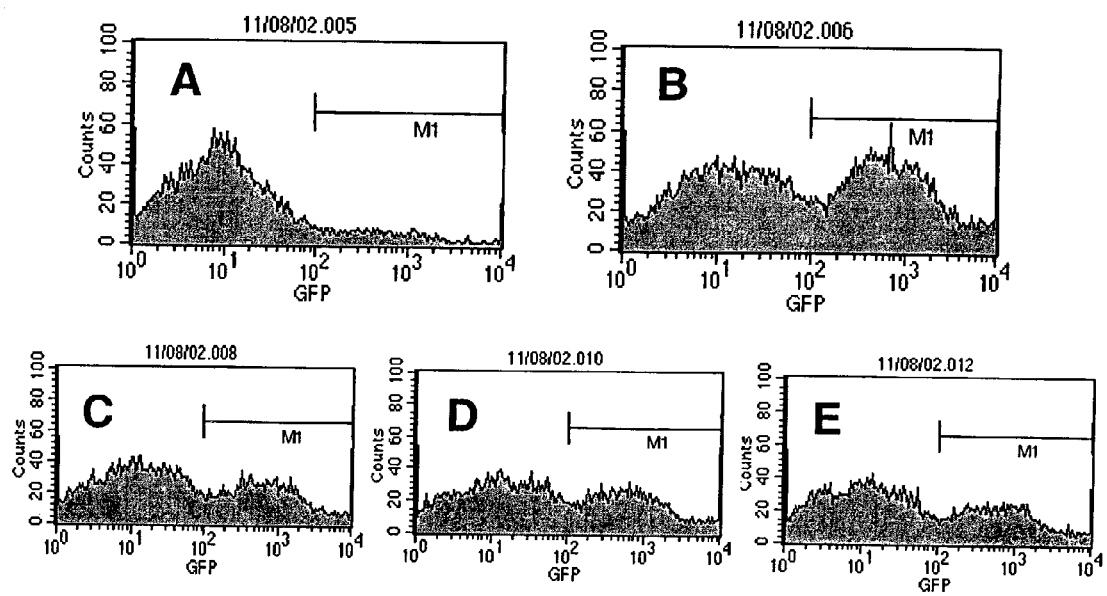
FIG. 15A is a histograms of green fluorescence (FL-1-H) of PE-anti-CD11c positive cells of vehicle-sensitized ears from control mice
FIG. 15B is a histogram of green fluorescence (FL-1-H) of PE-anti-CD11c positive cells of FITC-sensitized ears.
FIG. 15C is a histogram of green fluorescence (FL-1-H) of PE-anti-CD11c positive cells of FITC-sensitized ears from mice pre-treated with 50 mg/kg 4-F-GlcNAc.
FIG. 15D is a histogram of green fluorescence (FL-1-H) of PE-anti-CD11c positive cells of FITC-sensitized ears from mice pre-treated with 100 mg/kg 4-F-GlcNAc.
FIG. 15E is a histogram of green fluorescence (FL-1-H) of PE-anti-CD11c positive cells of FITC-sensitized ears from mice pre-treated with 250 mg/kg 4-F-GlcNAc.

Results from contact hypersensitivity experiments show that 4-F-GlcNAc treatment (50–250 mg/kg/day×6) can prevent the elicitation/efferent phase and lymphocytic infiltration of the antigen-dependent inflammatory response. However, 4-F-GlcNAc treatment could have affected the afferent phase of this inflammatory response by inhibiting the migration of epidermal antigen-presenting LC from the epidermis to draining lymph nodes preventing processing and presentation of contact sensitizing agent and antigen-specific T-cell activation within draining lymph nodes. To investigate the effects of 4-F-GlcNAc on this process, we analyzed the capacity of epidermal LC to migrate to respective draining lymph nodes and present contact sensitizing agent, 0.5% FITC after 3 day i.p. treatments with 4-F-GlcNAc. Following a 30 h incubation, CD11c-positive LC isolated from the draining lymph nodes were analyzed for FITC expression by flow cytometry. A similar proportion of CD11c-positive LC were labeled with FITC, when comparing saline-pretreated mice to mice pretreated with 50, 100, or 250 mg/kg/day×3 (FIG. 15). Moreover, there was no dose-response relationship related to 4-F-GlcNAc treatment and frequency of DC presenting FITC (FIG. 15). However, mice receiving 250 mg/kg/day during the 4-day experiment did not show similar weight gain (i.e. a cumulative dose of 750 mg/kg was growth inhibitory) compared with other mice that received cumulative doses of 0, 150 or 300 mg/kg, suggesting that a 3-day pretreatment schedule was sufficient time for 4-GlcNAc to potentially elicit anti-migratory effects. These data indicate that 4-F-GlcNAc, at doses that prevented the elicitation phase of delayed-type contact hypersensitivity, did not influence the afferent aspect or sensitization phase of the immunological response.

REFERENCES

1. Picker L J, Michie S A, Rott L S, Butcher E C. A unique phenotype of skin-associated lymphocytes in humans. Preferential expression of the HECA-452 epitope by benign and malignant T cells at cutaneous sites. Amer. J. Path. 1990;136:1053–1068.
2. Berg E L, Yoshino T, Rott L S, et al. The cutaneous lymphocyte antigen is a skin lymphocyte homing receptor for the vascular lectin endothelial cell-leukocyte adhesion molecule 1. J. Exp. Med. 1991;174:1461–1466.
3. Fuhlbrigge R C, Kieffer D, Armerding D, Kupper T S. Cutaneous lymphocyte antigen is a specialized form of PSGL-1 expressed on skin-homing T-cells. Nature. 1997; 389:978–981.
4. Davis R E, Smoller B R. T-lymphocytes expressing HECA-452 epitope are present in cutaneous acute graft versus host disease and erythema multiforme, but not in acute graft versus host disease in gut organs. Amer. J. Path. 1992;141(3):691–698.
5. Borowitz M J, Weidner A, Olsen E A, Picker L J. Abnormalities of circulating T-cell subpopulations in patients with cutaneous T-cell lymphoma: cutaneous lymphocyte-associated antigen expression on T cells correlates with extent of disease. Leukemia. 1993;7(6):859–63.
6. Rossiter H, Reijsen F V, Mudde G C, et al. Skin disease-related T-cells bind to endothelial selectins: expression of cutaneous lymphocyte antigen (CLA) predicts E-selectin but not P-selectin binding. Eur. J. Immuno. 1994;24: 205–210.
7. Rook A H, Heald P. The immunopathogenesis of cutaneous T-cell lymphoma. Hemato. Oncol. Clin. N. Amer. 1995;9:997–1010.
8. Santamaria Babi L F, Picker L J, Perez Soler M T, et al. Circulating allergen-reactive T cells from patients with atopic dermatitis and allergic contact dermatitis express the skin-selective homing receptor, the cutaneous lymphocyte-associated antigen. J. Exp. Med. 1995;181(5): 1935–40.
9. Robert C, Kupper T S. Inflammatory skin diseases, T cells, and immune surveillance. New EngL. J. Med. 1999;341 (24):1817–28.
10. Sigmundsdottir H, Gudjonsson J E, Jonsdottir I, Ludviksson B R, Valdimarsson H. The frequency of CLA+ CD8+ T cells in the blood of psoriasis patients correlates closely with the severity of their disease. Clin. Exp. Immunol. 2001;126(2):365–369.

1. Borges E, Pendl G, Eytner R, Steegmaier M, Zollner 0, Vestweber D. P-selectin glycoprotein ligand-1 (PSGL-1) on T helper 1 but not on T helper 2 cells binds to P-selectin and supports migration into inflamed skin. J. Biol. Chem. 1997;272(45):28786–92.

2. Kieffer J D, Fuhlbrigge R C, Armerding D, et al. Neutrophils, monocytes, and dendritic cells express the same specialized form of PSGL-1 as do skin-homing memory T cells: cutaneous lymphocyte antigen. Biochem. Biophys. Res. Commun. 2001;285(3):577–87.

3. Tu L, Murphy P G, Li X, Tedder T F. L-selectin ligands expressed by human leukocytes are HECA-452 antibody-defined carbohydrate epitopes preferentially displayed by P-selectin glycoprotein ligand-1. J. Immunol. 1999; 163 (9):5070–8.

4. Blander J M, Visintin I, Janeway C A Jr, Medzhitov R. Alpha(1,3)-fucosyltransferase VII and alpha(2,3)-sialyltransferase IV are up-regulated in activated CD4 T cells and maintained after their differentiation into Th1 and migration into inflammatory sites. J. Immunology. 1999; 163(7):3746–3752.

5. Zeng S, Gallego R G, Dinter A, et al. Complete enzymatic synthesis of the mucin-type sialyl Lewis X epitope, involved in the interaction between PSGL-1 and P-selectin. Glycoconjugate J. 1999;16(9):487–97.

6. Lowe J B, Stoolman L M, Nair R P, Larsen R D, Berhend T L, Marks RM. ELAM-1--dependent cell adhesion to vascular endothelium determined by a transfected human fucosyltransferase cDNA. Cell. 1990;63(3):475–484

7. Wagers A J, Lowe J B, Kansas G S. An important role for the alpha 1,3 fucosyltransferase, FucT-VII, in leukocyte adhesion to E-selectin. Blood. 1996;88(6):2125–2132.

8. Maly P, Thall A, Petryniak B, et al. The alpha(1,3) fucosyltransferase Fuc-TVII controls leukocyte trafficking through an essential role in L-, E-, and P-selectin ligand biosynthesis. Cell. 1996;86:643–653.

9. Niemela R, Natunen J, Majuri M L, et al. Complementary acceptor and site specificities of Fuc-TIV and Fuc-TVII allow effective biosynthesis of sialyl-TriLex and related polylactosamines present on glycoprotein counterreceptors of selectins. J. Biol. Chem. 1998;273(7): 4021–4026.

20. Okajima T, Fukumoto S, Miyazaki H, et al. Molecular cloning of a novel alpha2,3-sialyltransferase (ST3Gal VI) that sialylates type II lactosamine structures on glycoproteins and glycolipids. J. Biol. Chem. 1999;274(17):11479–11486.

21. Weninger W, Ulfman L H, Cheng G, et al. Specialized contributions by alpha(1,3)-fucosyltransferase-IV and FucT-VII during leukocyte rolling in dermal microvessels. Immunity. 2000;12(6):665–76.

22. Homeister J W, Thall A D, Petryniak B, et al. The alpha(1,3)fucosyltransferases FucT-IV and FucT-VII exert collaborative control over selectin-dependent leukocyte recruitment and lymphocyte homing. Immunity. 2001;15(1):115–126.

23. Mizukawa Y, Shitara K, Yamazaki Y, Kudo T, Narimatsu H, Shiohara T. Immunohistochemical detection of skin-homing T cells expressing fucosyltransferase VII (Fuc-TVII) in vitro and in situ. Lab. Invest. 2001;81(5):771–773.

24. Nakayama F, Teraki Y, Kudo T, et al. Expression of cutaneous lymphocyte-associated antigen regulated by a set of glycosyltransferases in human T cells: involvement of alpha1, 3-fucosyltransferase VII and beta1,4-galactosyltransferase I. J. Invest. Dermatol. 2000;115(2):299–306.

25. Nakamura M, Furukawa Y, Sasaki R, et al. UDP-GlcNAc:Galbeta 1→3GalNAc (GlcNAc to GalNAc) beta1→6N-acetylglucosaminyltransferase holds a key role on the control of CD15s expression in human pre-B lymphoid cell lines. Glycobiology. 1999;9(1):1–12.

26. Kumar R, Camphausen R T, Sullivan F X, Cumming D A. Core2 beta-1,6-N-acetylglucosaminyltransferase enzyme activity is critical for P-selectin glycoprotein ligand-1 binding to P-selectin. Blood. 1996;88:3872–3879.

27. Ellies L G, Tsuboi S, Petryniak B, Lowe J B, Fukuda M, Marth J D. Core 2 oligosaccharide biosynthesis distinguishes between selectin ligands essential for leukocyte homing and inflammation. Immunity. 1998;9(6):881–90.

28. Snapp K R, Heitzig C E, Ellies L G, Marth J D, Kansas G S. Differential requirements for the O-linked branching enzyme core 2 betal-6-N-glucosaminyltransferase in biosynthesis of ligands for E-selectin and P-selectin. Blood. 2001;97(12):3806–11.

29. Sperandio M, Thatte A, Foy D, Ellies L G, Marth J D, Ley K. Severe impairment of leukocyte rolling in venules of core 2 glucosaminyltransferase-deficient mice. Blood. 2001;97(12):3812–3819.

30. Moore K L, Eaton S F, Lyons D E, Lichenstein H S, Cummings R D, McEver R P. The P-selectin glycoprotein ligand from human neutrophils displays sialylated, fucosylated, O-linked poly-N-acetyllactosamine. J. Biol. Chem. 1994;269(37):23318–27.

31. Bernacki R J, Sharma M, Porter NK, Rustum Y, Paul B, Korythyk W. Biochemical characteristics, metabolism, and antitumor activity of several acetylated hexosamines. J. Supramol. Struct. 1977;7(2):235–50.

32. Sharma M, Bernacki R J, Paul B, Korytnyk W. Fluorinated carbohydrates as potential plasma membrane modifiers. Synthesis of 3-deoxy-3-fluoro derivatives of 2-acetamido-2-deoxy-D-hexopyranoses. Carbohyd. Res. 1990;198:205–221.

33. Woynarowska B, Skrincosky D M, Haag A, Sharma M, Matta K L, Bernacki R J. Inhibition of lectin-mediated ovarian tumor cell adhesion by sugar analogs. J. Biol. Chem. 1994;269(36):22797–22803.

34. Woynarowska B, Dimitroff C J, Skrincosky D. M, Sharma M, Matta K L, Bernacki R J. The effect of a 4-fluoro-glucosamine analog on the adhesion of human colon carcinoma HT-29 cells. Glycoconjugate J. 1996; 13(4):663–674.

35. Sackstein R, Dimitroff C J. A hematopoietic cell L-selectin ligand that is distinct from PSGL-1 and displays N-glycan-dependent binding activity. Blood. 2000;96: 2765–2774.

36. Dimitroff C J, Lee J, Fuhlbrigge R C, Sackstein R. A distinct glycoform of CD44 is an L-selectin ligand on human hematopoietic progenitor cells. Proc. Natl. Acad. Sci. 2000;97(25), 13841–13846.

37. Dimitroff C J, Lee J Y, Rafii S, Fuhlbrigge R C, Sackstein R. CD44 is a major E-selectin ligand on human hematopoietic progenitor cells. J. Cell Biol. 2001; 153:1277–1286.

38. Dimitroff C J, Lee J Y, Schor K, Sandmaier B, Sackstein R. Differential L-selectin binding activities of human hematopoietic cell L-selectin ligands, HCELL and PSGL-1. J. Biol. Chem. 2001;276(50):47623–47631.

39. Kuan S F, Byrd J C, Basbaum C, Kim Y S. Inhibition of mucin glycosylation by aryl-N-acetyl-alpha-galactosamides in human colon cancer cells. J. Biol. Chem. 1989; 264(32):19271–7.
40. Stroud M R, Handa K, Salyan M E, et al. Monosialogangliosides of human myelogenous leukemia HL60 cells and normal human leukocytes. 1. Separation of E-selectin binding from nonbinding gangliosides, and absence of sialosyl-Le(x) having tetraosyl to octaosyl core. Biochemistry. 1996;35(3):758–69.
41. Pinola M, Renkonen R, Majuri M L, Tiisala S, Saksela E. Characterization of the E-selectin ligand on NK cells. J. Immunol. 1994;152(7):3586–94.
42. Alon R, Rossiter H, Wang X, Springer T A, Kupper T S. Distinct cell surface ligands mediate T lymphocyte attachment and rolling on P and E selectin under physiological flow. J. Cell Biol. 1994;127(5):1485–95.
43. Snapp K R, Wagers A J, Craig R, Stoolman L M, Kansas G S. P-selectin glycoprotein ligand-1 is essential for adhesion to P-selectin but not E-selectin in stably transfected hematopoietic cell lines. Blood. 1997;89(3):896–901.
44. Burdick M M, Bochner B S, Collins B E, Schnaar R L, Konstantopoulos K. Glycolipids support E-selectin-specific strong cell tethering under flow. Biochem. Biophys. Res. Commun. 2001;284(1):42–9.
45. Piller F, Le Deist F, Weinberg K I, Parkman R, Fukuda M. Altered O-glycan synthesis in lymphocytes from patients with Wiskott-Aldrich syndrome. J Exp. Med. 1991;173(6):1501–10
46. Schmid K, Hediger M A, Brossmer R, et al. Amino acid sequence of human plasma galactoglycoprotein: identity with the extracellular region of CD43 (sialophorin). Proc. Natl. Acad. Sci. USA. 1992;89(2):663–7.
47. Heald P W, Yan S L, Edelson R L, Tigelaar R, Picker L J. Skin-selective lymphocyte homing mechanisms in the pathogenesis of leukemic cutaneous T-cell lymphoma. J. Invest. Dermatol. 1993;101(2):222–6.
48. Picker L J, Treer J R, Ferguson-Darnell B, Collins P A, Bergstresser P R, Terstappen L W. Control of lymphocyte recirculation in man. II. Differential regulation of the cutaneous lymphocyte-associated antigen, a tissue-selective homing receptor for skin-homing T cells. J. Immunol. 1993;150(3):1122–36.
49. Tanaka Y, Wake A, Horgan K J, et al. Distinct phenotype of leukemic T cells with various tissue tropisms. J. Immunol. 1997;158(8):3822–9.
50. Erdmann I, Scheidegger E P, Koch F K, et al. Fucosyltransferase VII-deficient mice with defective E-, P-, and L-selectin ligands show impaired CD4+ and CD8+ T cell migration into the skin, but normal extravasation into visceral organs. J. Immunol. 2002;168(5):2139–46.
51. Maemura K, Fukuda M. Poly-N-acetyllactosaminyl O-glycans attached to leukosialin. The presence of sialyl Le(x) structures in O-glycans. J. Biol. Chem. 1992;267 (34):24379–86.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inhibiting migration of one or more leukocytes comprising contacting one or more leukocytes with a fluorinated N-acetylglucosamine.
2. The method of claim 1, wherein said N-acetylglucosamine is 2-acetamido-2-deoxy-1,3,6-tri-O-acetyl-4-deoxy-4-fluoro-D-glucopyranose or 2-acetamido-2-deoxy-1,4,6-tri-O-acetyl-3-deoxy-3-fluoro-D-glucopyranose.
3. The method of claim 1, wherein said one or more leukocytes comprise a lymphoid cell.
4. The method of claim 3, wherein said lymphoid cell is a T-cell.
5. The method of claim 4, wherein said T cell is a Th1 cell.
6. The method of claim 1, wherein said one or more leukocytes comprise a leukemic cell.
7. The method of claim 1, wherein said one or more leukocytes comprise a lymphoma cell.
8. The method of claim 7, wherein said lymphoma cell is cutaneous lymphoma cell.
9. The method of claim 1, wherein said N-acetylglucosamine is present at the concentration of 0.05 mM to 0.5 mM.
10. The method of claim 1, wherein leukocytes are contacted with a fluorinated N-acetylglucosamine in a subject to which the fluorinated N-acetylglucosamine is administered.
11. The method of claim 10, wherein the fluorinated N-acetylglucosamine is administered to the subject such that inflammation is inhibited in a tissue in the subject.
12. The method of claim 11, wherein the tissue is a dermal tissue.
13. The method of claim 11, wherein the inflammation is chronic inflammation.
14. The method of claim 13, wherein the chronic inflammation is delayed type hypersensitivity.
15. The method of claim 11, wherein the inflammation is acute inflammation.
16. The method of claim 11, wherein the inflammation is cutaneous inflammation.
17. The method of claim 11, wherein the inflammation is psoriasis.
18. The method of claim 11, wherein the subject suffers from or is at risk of an inflammatory bowel disease.
19. The method of claim 11, wherein the subject is further administered an anti-inflammatory compound.
20. The method of claim 19, wherein the anti-inflammatory compound is selected from the group consisting of aspirin, ibuprofen, naproxen sodium (Alleve), celecoxib, prednisone, prednisolone, and dexamethasone.
21. The method of claim 11, wherein the subject is administered the fluorinated N-acetylglucosamine prior to an inflammatory event.
22. The method of claim 11, wherein the subject is administered the fluorinated N-acetylglucosamine during an inflammatory event.
23. The method of claim 11, wherein the subject is administered the fluorinated N-acetylglucosamine by a route selected from the group consisting of intraperitoneal, subcutaneous, nasal, intravenous, oral, topical and transdermal delivery.
24. The method of claim 10, wherein the subject is administered less than 50 mg/kg of the fluorinated N-acetylglucosamine.
25. The method of claim 18, wherein the inflammatory bowel disease is colitis or Crohn's disease.
26. The method of claim 18, wherein the subject suffers from an inflammatory bowel disease.

* * * * *

UNITED STATES PATENT AND TRADEMARK OFFICE
CERTIFICATE OF CORRECTION

PATENT NO. : 7,098,195 B2
APPLICATION NO. : 10/305812
DATED : August 29, 2006
INVENTOR(S) : Robert Sackstein et al.

It is certified that error appears in the above-identified patent and that said Letters Patent is hereby corrected as shown below:

Title Page Item (56), OTHER PUBLICATIONS, reference Dimitroff CJ, et al.:
 delete "Electin" and replace with --Selectin--

Page 2 Item (56), OTHER PUBLICATIONS, reference Snapp KR, et al.:
 delete "(2001." And replace with --(2001). --

Page 2 Item (56), OTHER PUBLICATIONS, reference Thomas et al.:
 delete "fluro-$\alpha$" (second occurrence) -- fluro-$\beta$ --
 delete "deoxy-$\beta$" and replace with -- deoxy-$\alpha$ --

Page 2 Item (56), OTHER PUBLICATIONS, reference Zeng S. et al.:
 delete "*GLycoconjugate*" and replace with -- Glycoconjugate --

Signed and Sealed this

Eighteenth Day of December, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,098,195 B2 |
| APPLICATION NO. | : 10/305812 |
| DATED | : August 29, 2006 |
| INVENTOR(S) | : Robert Sackstein et al. |

Page 1 of 1

It is certified that error appears in the above-identified patent and that said Letters Patent is hereby corrected as shown below:

Col. 1, line 4;
After the title and before the background of the invention, please add the following paragraph:

STATEMENT AS TO FEDERALLY SPONSORED RESEARCH

This invention was made with Government support under Grant Nos. CA084156, CA016056, CA070853, and HL060528 awarded by the National Institutes of Health. The Government has certain rights in this invention.

Signed and Sealed this

Twenty-first Day of July, 2009

JOHN DOLL
*Acting Director of the United States Patent and Trademark Office*